(12) United States Patent
Wooley et al.

(10) Patent No.: US 9,173,972 B2
(45) Date of Patent: Nov. 3, 2015

(54) METHODS AND COMPOSITIONS FOR PROMOTING WOUND HEALING

(71) Applicants: The University of Georgia Research Foundation, Inc., Athens, GA (US); Sandra L Wooley, Athens, GA (US)

(72) Inventors: Richard E. Wooley, Athens, GA (US); Branson W. Ritchie, Athens, GA (US); Douglas T. Kemp, Watkinsville, GA (US); Anthony C. Capomacchia, Statham, GA (US); Victoria V. Burnley, Watkinsville, GA (US)

( * ) Notice: Subject to any disclaimer, the term of this patent is extended or adjusted under 35 U.S.C. 154(b) by 0 days.

(21) Appl. No.: 14/711,224

(22) Filed: May 13, 2015

(65) Prior Publication Data
US 2015/0246155 A1    Sep. 3, 2015

Related U.S. Application Data

(63) Continuation of application No. 11/173,824, filed on Jul. 1, 2005.

(51) Int. Cl.
| | |
|---|---|
| *A61K 31/198* | (2006.01) |
| *A61K 31/133* | (2006.01) |
| *A61K 33/38* | (2006.01) |
| *A61K 45/06* | (2006.01) |
| *A61L 26/00* | (2006.01) |

(52) U.S. Cl.
CPC ........... *A61L 26/0066* (2013.01); *A61K 31/133* (2013.01); *A61K 31/198* (2013.01); *A61K 33/38* (2013.01); *A61K 45/06* (2013.01); *A61L 26/00* (2013.01); *A61L 2300/406* (2013.01)

(58) Field of Classification Search
CPC ... A61K 31/195; A61K 9/0014; A61K 33/38; A61K 31/133; A61K 31/198; A61L 26/0066; A61L 26/00
See application file for complete search history.

(56) References Cited

U.S. PATENT DOCUMENTS

| | | |
|---|---|---|
| 3,049,474 A | 8/1962 | Hepworth |
| 3,091,569 A | 5/1963 | Sheffner |
| 3,758,682 A | 9/1973 | Huber et al. |
| 4,122,158 A | 10/1978 | Schmitt |
| 4,258,056 A | 3/1981 | Lentsch |
| 4,323,558 A | 4/1982 | Nelson |

(Continued)

FOREIGN PATENT DOCUMENTS

| | | |
|---|---|---|
| CA | 2 384 881 A1 | 3/2001 |
| EP | 0 603 406 A1 | 6/1994 |

(Continued)

OTHER PUBLICATIONS

Friedman, C., et al., "Key Considerations for Utilizing Sliver Dressings," Podiatry Today 19(5):24-29, May 2006.

(Continued)

*Primary Examiner* — Rachael E Bredefeld
(74) *Attorney, Agent, or Firm* — Patrick D. Lowder; Smith Risley Tempel Santos LLC

(57) ABSTRACT

The present invention provides methods and compositions that use the combination of Tris and EDTA to inhibit the growth of microorganisms at the site of a wound or burn, and/or to promote the healing of a wound or burn, and/or to reduce the sensation of pain at the site of a wound or burn. The amount of Tris and EDTA applied to a wound or burn can be selected to achieve one or more of the foregoing effects.

10 Claims, 3 Drawing Sheets

(56) References Cited

U.S. PATENT DOCUMENTS

| | | |
|---|---|---|
| 4,438,099 A | 3/1984 | Azzariti |
| 4,485,091 A | 11/1984 | Fitton |
| 4,939,135 A | 7/1990 | Robertson |
| 4,945,110 A | 7/1990 | Brokken et al. |
| 4,983,585 A | 1/1991 | Pennell |
| 5,004,607 A | 4/1991 | Ragland et al. |
| 5,055,447 A | 10/1991 | Palladino et al. |
| 5,064,647 A | 11/1991 | Storm |
| 5,098,417 A | 3/1992 | Yamazaki et al. |
| 5,135,910 A | 8/1992 | Blackburn et al. |
| 5,160,737 A | 11/1992 | Friedman et al. |
| 5,227,157 A | 7/1993 | McGinity et al. |
| 5,260,292 A | 11/1993 | Robinson |
| 5,364,638 A | 11/1994 | Sugo |
| 5,455,266 A | 10/1995 | Kusuda et al. |
| 5,489,430 A | 2/1996 | Saito et al. |
| 5,565,189 A | 10/1996 | Mulder |
| 5,604,200 A | 2/1997 | Taylor-McCord |
| 5,621,076 A | 4/1997 | Kodama et al. |
| 5,624,704 A | 4/1997 | Darouiche et al. |
| 5,646,151 A | 7/1997 | Kruse et al. |
| 5,688,516 A | 11/1997 | Raad et al. |
| 5,698,207 A | 12/1997 | Staats |
| 5,744,155 A | 4/1998 | Friedman et al. |
| 5,753,614 A | 5/1998 | Blackburn |
| 5,760,026 A | 6/1998 | Blackburn et al. |
| 5,762,917 A | 6/1998 | Osborne |
| 5,766,594 A | 6/1998 | Kodama et al. |
| 5,848,700 A | 12/1998 | Horn |
| 5,858,962 A | 1/1999 | Blackburn et al. |
| 5,863,938 A | 1/1999 | Martin |
| 5,914,113 A | 6/1999 | Schrier |
| 5,942,232 A | 8/1999 | Costa |
| 5,958,443 A | 9/1999 | Viegas |
| 6,086,892 A | 7/2000 | Cook |
| 6,159,945 A | 12/2000 | Wu |
| 6,165,484 A | 12/2000 | Raad et al. |
| 6,207,411 B1 | 3/2001 | Ross et al. |
| 6,207,679 B1 | 3/2001 | Cuny |
| 6,224,853 B1 | 5/2001 | Steel |
| 6,267,979 B1 | 7/2001 | Raad et al. |
| 6,270,770 B1 | 8/2001 | Schrier et al. |
| 6,270,781 B1 | 8/2001 | Gehlsen |
| 6,291,656 B1 | 9/2001 | Wu |
| 6,413,556 B1 | 7/2002 | Bathurst et al. |
| 6,414,023 B1 | 7/2002 | Brandsborg et al. |
| 6,423,299 B1 | 7/2002 | Fischetti |
| 6,509,319 B1 | 1/2003 | Raad et al. |
| 6,509,979 B2 | 1/2003 | Raad et al. |
| 6,518,252 B2 | 2/2003 | Wooley et al. |
| 6,538,155 B1 | 3/2003 | Melman |
| 6,723,688 B1 | 4/2004 | Malik et al. |
| 2002/0091074 A1 | 7/2002 | Wooley et al. |
| 2002/0098208 A1 | 7/2002 | Wooley et al. |
| 2003/0032573 A1 | 2/2003 | Tanner |
| 2003/0032605 A1 | 2/2003 | Raad et al. |
| 2003/0203046 A1 | 10/2003 | Burrell et al. |
| 2003/0220302 A1 | 11/2003 | Kohan et al. |
| 2004/0151765 A1 | 8/2004 | Ritchie et al. |
| 2004/0208842 A1 | 10/2004 | Ritchie et al. |
| 2005/0061678 A1 | 3/2005 | Holladay et al. |

FOREIGN PATENT DOCUMENTS

| | | |
|---|---|---|
| GB | 1 539 771 | 2/1979 |
| WO | WO 95/30751 | 11/1995 |
| WO | 99/09997 A1 | 3/1999 |
| WO | WO 99/21866 | 5/1999 |
| WO | 00/00186 A1 | 1/2000 |
| WO | 02/24143 A2 | 3/2002 |
| WO | WO2004/028461 | 4/2004 |
| WO | 2006/074117 A2 | 7/2006 |

OTHER PUBLICATIONS

Schosinsky, K.H , et al., "Micromethod for Analysis for Chloride in Physiological Fluids," Clinical Chemistry 22(8):1339-1342, May 1976.

Farca, A.M., et al., "Potentiation of Antibiotic Activity by EDTA-Tromethamine Against Three Clinically Isolated Gram-Positive Resistant Bacteria. An In Vitro Investigation," Veterinary Research Communications 18(1):1-6, Jan. 1994.

Kaur, P and D.V. Vadehra, "Effect of Certain Chelating Agents on the Antibacterial Action of Silver Nitrate," Journal of Hygiene, Epidemiology, Microbiology and Immunology 32(4299-305, 1988.

Alekshun, M.N., and S.B. Levy, "Regulation of Chromosomally Mediated Multiple Antibiotic Resistance: The *mar* Regulon," *Antimicrobial Agents and Chemotherapy* 41(10):2067-2075, Oct. 1997.

Ashworth, C.D., and D.R. Nelson, "Antimicrobial Potentiation of Irrigation Solutions Containing Tris-[Hydroxymethyl] Aminomethane-EDTA," *Journal of American Veterinary Medical Association* 197(11):1513-1514, Dec. 1, 1990.

Bayer, M.E., and L. Leive, "Effect of Ethlyenediamintetraacetate Upon the Surface of *Escherichia coli*," *Journal of Bacteriology* 130(3):1364-1381, Jun. 1977.

Biziulevichius, G.A. and K. Lukauskas, "In Vivo Studies on Lysosubtilin. 3. Efficacy for Treatment of Mastitis and Superficial Lesions of the Udder and Teats in Cows," *Vet. Research* 29:441-456, 1998.

Bjorling, D.E., and R.E. Wooley, "EDTA-Tromethamine Lavage as an Ajunct Treatment for Multiple Fistulas in a Dog," *Journal of American Veterinary Medical Association* 181(6):596-597, Sep. 15, 1982.

Blair, J.E., et al., *Manual of Clinical Microbiology*, American Society for Microbiology, Williams & Wilkins, Baltimore, 1980, p. 307.

Blue, J.L., et al, "Treatment of Experimentally Induced *Pseudomonas aeruginosa* Otitis Externa in the Dog by Lavage with EDTA-Tromethamine- Lysozyme," *American Journal of Veterinary Research* 35(9):1221-1223, Sep. 1974.

Brouillete, et al., "Mouse Mastitis Model of Infection for Antimicrobial Compound Efficacy Studies Against Intracellular and Extracellular Forms of *Staphylococcus aureus*," *Veterinary Microbiology* 101:253-262, 2004.

Brown, M.R.W., and R.M.E. Richards, "Effect of Ethylenediamine Tetraacetate on the Resistance of *Pseudomonas aeruginosa* to Antibacterial Agents," *Nature* (London) 207(5004):1391-1393, Sep. 25, 1965.

Bryan, L.E., *Antimicrobial Drug Resistance*, Academic Press, New York, 1984, pp. 255-256.

Chew, B.P., et al., In Vitro Growth Inhibition of Mastitis Causing Bacteria by Phenolics and Metal Chelators, *Journal of Dairy Science* 68:3037-3046, 1985.

Colman, P.M., Effects of Amino Acid Sequence Changes on Antibody-Antigen Interactions, *Res. Immunology* 145:33-36, Jan. 1994.

Cullor, J.S., "Antibiotic Residue Tests for Mammary Gland Secretions," *Veterinary Clinics of North America: Food Animal Practice* 9(3)609-620, Nov. 1993.

Dariclox®, valleyvet.com, Aug. 7, 2003, <http://www.valleyvet.com./ct_library_info.html?product . . . > [retrieved Feb. 20, 2004].

De Oliveira, A.P., et al., "Antimicrobial Susceptibility of *Staphylococcus aureus* Isolated From Bovine Mastitis in Europe and the United States," *Journal of Dairy Science* 83:855-862, Apr. 2000.

Devriese, L.A., et al., "Identification and Antimicrobial Susceptibility of *Staphylococcus chromogenes* Isolates From Intramammary Infections of Dairy Cows," *Veterinary Microbiology* 87:175-182, 2002.

Dodd, F.H., "Mastitis-Progress on Control," *Journal of Dairy Science* 66: 1773-1778, 1983.

Erskine, R.J., et al., "Advances in the Therapy for Mastitis," *Veterinary Clinics of North America: Food Animal Practice* 9(3):499-517, Nov. 1993.

Erskine, R.J, et al, "*Pseudomonas* Mastitis: Difficulties in Detection and Elimination From Contaminated Wash-Water Systems," *Journal of American Veterinary Medical Association* 191(7):811-815, Oct. 1987.

(56) References Cited

OTHER PUBLICATIONS

Farca, A.M., et al., "Potentiation of the In Vitro Activity of Some Antimicrobial Agents Against Selected Gram-Negative Bacteria by EDTA-Tromethamine,". *Veterinary Research Communications* 17:77-84, 1993.

Gander, S., "Bacterial Biofilms: Resistance to Antimicrobial Agents," *Journal of Antimicrobial Chemotherapy* 37:1047-1050, 1996.

Gerberick, G.F., and P.A. Castric, "In Vitro Susceptibility of *Pseudomonas aeruginosa* to Carbenicillin, Glycine, and Ethylenediaminetetraacetic Acid Combinations," *Antimicrobial Agents and Chemotherapy* 17(4):732-735, Apr. 1980.

Goldschmidt, M.C., and O. Wyse, "The Role of Tris in EDTA Toxicity and Lysozyme Lysis," *Journal Gen. Microbiology* 47:421-431, 1967.

Goldschmidt, M.C., et al., "EDTA and Lysozyme Lavage in the Treatment of *Pseudomonas* and Coliform Bladder Infections," *Journal of Urology* 107:969-972, 1972.

Greenspan, N.S., and E. Di Cera, "Defining Epitopes: It's Not as Easy as It Seems," *Nature Biotechnology* 17:936-937, Oct. 1999.

Gruet, P., et al., "Bovine Mastitis and Intramammary Drug Delivery: Review and Perspectives," *Advanced Drug Delivery Reviews* 50:245-259, 2001.

Hall, R.M., "Mobile Gene Cassettes and Integrons: Moving Antibiotic Resistance Genes in Gram-Negative Bacteria," *Ciba Foundation Symposium 207 / Antibiotic Resistance: Origins, Evolution, Selection and Spread*, Wiley, Chichester, UK, 1997, pp. 192-202.

Heppel, L.S., "The Concept of Periplasmic Enzymes" in L.I. Rothfield (ed.), *Structure and Function of Biological Membranes*, Academic Press, New York, 1972, pp. 224-247.

Jackson, E.R., "The Proper Use and Benefits of Veterinary Antimicrobial Agents in Practice in Cattle," *Veterinary Microbiology* 35(3-4):349-356, 1993.

Krieg, D.P., et al., "Phosphorylcholine Stimulates Capsule Formation of Phosphate-Limited Mucoid *Pseudomonas aeruginosa*," *Infection and Immunity* 56(4):864-873, Apr. 1988.

Lee, A.H., et al., "Effects of Gentamicin Solution and Cream on the Healing of Open Wounds," *American Journal of Veterinary Research* 45(8):1487-1492, Aug. 1984.

Leive, L., "A Nonspecific Increase in Permeability in *Escherichia coli* Produced by EDTA," *Proceedings of the National Academy of Science USA* 53:745-750, 1965.

Leive., L., and V.K. Shovlin, "Physical, Chemical, and Immunological Properties of Lipopolysaccharide Released From *Escherichia coli* by Ethylenediaminetetraacetate," *Journal of Biological Chemistry* 243(24): 6384-6391, Dec. 1968.

Minister, P., "Two New Antibiotics to Combat Mastitis," *The Farmer* 1(4): 31-32, 1976.

Monkhouse, D.C., and G.A. Groves, "The Effect of EDTA on the Resistance of *Pseudomonas aeruginosa* to Benzalkonium Chloride," *Australian Journal of Pharmacology* 48(570):570-575, Jun. 1967.

Nicholas, R.A.J., and R.D. Ayling, "*Mycoplasma bovis*: Disease, Diagnosis, and Control," *Research in Veterinary Science* 74:105-112, 2003.

Pirsue® Sterile Solution, *Product Brochure*, Pharmacia & Upjohn Company, Kalamazoo, Michigan, Jan. 2003 (product brochure).

Rebhun, W.C., "Diseases of the Teats and Udder," *Diseases of Dairy Cattle*, Williams and Wilkins, Baltimore, 1995, pp. 279-308.

Roberts, N.A., et al., "The Bactericidal Action of Ethylenediaminetetra-Acetic Acid on *Pseudomonas aeruginosa*," *Microbios* 2(7-8):189-208, 1970.

Russell, A.D., "Effect of Magnesium Ions and Ethylenediamine Tetra-Acetic Acid on the Activity of Vancomycin Against *Escherichia coli* and *Staphylococcus aureus*," *Journal of Applied Bacteriology* 30(2):395-401, 1967.

Sabath, L.D., "Synergy of Antibacterial Substances by Apparently Known Mechanisms," *Antimicrobial Agents and Chemotherapy*, 1967, pp. 210-217.

Sambrook, J., et al. (eds.), "Appendix B.16: Preparation of Reagents and Buffers Used in Molecular Cloning," *Molecular Cloning: A Laboratory Manual*, 2d ed., Cold Spring Harbor Laboratory Press, New York, 1989.

Sandvang, D., et al., "Characterization of Integrons and Antibiotic Resistance Genes in Danish Multiresistant *Salmonella enterica Typhimurium DT104*," *FEMS Microbiology Letters* 160:37-41, 1998.

Smith, K.L, and J.S. Hogan, "Environmental Mastitis," *Veterinary Clinics of North America: Food Animal Practice* 9(3):489-498, Nov. 1993.

Sparks, T.A., et al., "Antimicrobial Effect of Combinations of EDTA-Tris and Amikacin or Neomycin on the Microorganisms Associated With Otitis Externa in Dogs," *Veterinary Research Communications* 18:241-249, 1994.

Sree, R.K., et al., "The Effects of Drugs on Wound Healing—Part II. Specific Classes of Drugs and Their Effect on Healing Wounds," *International Journal of Dermatology* 39:321-333, 2000.

Stern, G.A., et al., "Effect of Topical Antibiotic Solutions on Corneal Epithelial Wound Healing," *Archives of Ophthalmology* 101(4):644-647, Apr. 1983.

Tarabla, H., and V. Canavesio, "Prevalence of Intramammary Infections by Major Pathogens at Parturition in Dairy Cows After Intramuscular Antibiotic Therapy at Drying-Off: A Preliminary Report," *Journal of Dairy Research* 70:233-235, 2003.

Tsolov, D., et al., "Rifamycin Depot Syringae Intramammariae," *MBI-Medico-Biologic Information* 12:21-27, 1988.

Tyler, et al., "Treatment of Subclinical Mastitis," *Veterinary Clinics of North America: Food Animal Practice* 8(1):17-28, Mar. 1992.

Wooley, R.E., and J.L. Blue, "In Vitro Effect of EDTA-Tris-Lysozyme Solutions on Selected Pathogenic Bacteria," *Journal of Medical Microbiology* 8: 189-194, Jul. 1974.

Wooley, R.E., and M.S. Jones, "Action of EDTA-Tris and Antimicrobial Agent Combinations on Selected Pathogenic Bacteria," *Veterinary Microbiology* 8:.271-280, 1983.

Wooley, R.E., et al., "Antibiotic-Tromethamine-EDTA Lavage for the Treatment of Bacterial Rhinitis in a Dog," *Journal of American Veterinary Medical Association* 175:817-818, Oct. 1979.

Wooley, R.E., et al., "Attempt to Induce *Pseudomonas Pyoderma* in the Dog," *American Journal of Veterinary Research* 35(6):807-810, Jun. 1974.

Wooley, R.E., et al., "Attempted Reversal of Oxytetracycline Resistance of *Proteus mirabilis* by EDTA-Tromethamine Lavage in Experimentally Induced Canine and Feline Cystitis," *American Journal of Veterinary Research* 36(10):1533-1535, Oct. 1975.

Wooley, R.E., et al., "Effect of EDTA-Tris on an *Escherichia coli* Isolate Containing R Plasmids," *Veterinary Microbiology* 12:65-75, 1986.

Wooley, R.E., et al., "Efficacy of EDTA-Tris-Lysozyme Lavage in the Treatment of Experimentally Induced *Pseudomonas aeruginosa* Cystitis in the Dog," *American Journal of Veterinary Research* 35(1):27-29, Jan. 1974.

Wooley, R.E., et al., "In Vitro Action of Combinations of Antimicrobial Agents and EDTA-Tromethamine on *Escherichia coli*," *American Journal of Veterinary Research* 44(6):1154-1158, Jun. 1983.

Wooley, R.E., et al., "In Vitro Action of Combinations of Antimicrobial Agents With EDTA-Tromethamine on *Proteus vulgaris* of Canine Origin," *American Journal of Veterinary Research* 45(7):1451-1454, Jul. 1984.

Wooley, R.E., et al., "In Vitro Action of Combinations of Antimicrobial Agents and EDTA-Tromethamine on *Pseudomonas aeruginosa*," *American Journal of Veterinary Research* 44(8):1521-1524, Aug. 1983.

Wooley, R.E., et al., "In Vitro Effect of Combinations of Antimicrobial Agents and EDTA-Tromethamine on Certain Gram-Positive Bacteria," *American Journal of Veterinary Research* 44(11):2167-2169, Nov. 1983.

Wooley, R.E., et al., "In Vitro Effect of Ethylenediaminetetraacetic Acid-Tris on the Efficacy of Hatchery Disinfectants," *Avian Diseases* 44:901-906, 2000.

Wooley, R.E., et al., "In Vitro Evaluation of the Antimicrobial Effect of Commercially Available Mastitis Medications Combined with EDTA-Tris on Bacteria That Cause Mastitis in Cattle," *Veterinary Therapeutics* 3(2):150-156, 2002.

(56) References Cited

OTHER PUBLICATIONS

Wooley, R.E., et al., "Inhibitory Effects of Combinations of Oxytetracycline, Dimethyl Sulfoxide, and EDTA-Tromethamine on *Escherichia coli*," *American Journal of Veterinary Research* 42(11):2010-2013, Nov. 1981.

Wooley, R.E., et al., "Uptake of Antibiotics in Gram-Negative Bacteria Exposed to EDTA-Tris," *Veterinary Microbiology* 10(85):57-70, 1984.

Youngquist, R.S., "Pseudomonas Metritis in a Mare," *Veterinary Medicine/Small Animal Clinician* 70:340-342, Mar. 1975.

Yu, P. et al., "Inhibition of Alpha-Smooth Muscle Actin Expression in an In Vitro Wound Healing Model by Certain Antibiotics," *Journal of Trauma-Injury Infection and Critical Care* 47(1):130-135, Jul. 1999.

Yuen, D.E., and A.F. Stratford, "Vitamin A Activation of Transforming Growth Factor-Beta$_1$ Enhances Porcine Ileum Wound Healing In Vitro,"*Pediatric Research* 55(6):935-939, 2004.

Durst et al, "Tris/Tris HCL: A Standard Buffer for Use in the Physiologic pH Range," Clinical Chemistry, vol. 18, No. 3, 1972.

Dowsett. The use of silver-based dressings in wound care. Nursing Standard. 2004, 19(7), pp. 56-58 and 60.

Smith. Omental pedicle used to manage a large dorsal wound in a dog. Journal of Small Animal Practice. 1995, 36, pp. 267-270.

Lima, Ann et al. "Acute Toxicity of Silver to Selected Fish and Invertebrates," Bull. Environm. Contam. Toxicol. 29, 184-189 (1982).

METHODS AND COMPOSITIONS FOR PROMOTING WOUND HEALING

CROSS-REFERENCES TO RELATED APPLICATIONS

This application claims priority from, and incorporates by reference herein, U.S. application Ser. No. 11/173,824, filed Jul. 1, 2005.

FIELD OF THE INVENTION

This invention relates to methods and compositions for promoting the healing of wounds and burns.

BACKGROUND OF THE INVENTION

Wounds and burns involve the damage and death of tissue at the site of the wound or burn. Wounds and burns are susceptible to infection by microorganisms, such as bacteria and fungi. Microbial infection typically slows or prevents the healing of a wound or burn, and may lead to a localized or systemic infection of the wounded or burned organism. Antibiotic compositions are available to treat infections caused by many types of microorganisms, although, over time, microorganisms may become resistant to the antibiotics. The development of antibiotic resistant strains is a particular problem in hospitals and veterinary clinics where high levels of antibiotics are routinely used to treat infected people or animals. Additionally, many traditional antibiotics have undesirable side effects, such as damaging the sensory hairs within the mammalian ear, and thereby causing hearing loss. Moreover, many antibiotics may be irritating to the stomach when ingested, or may irritate a wound or burn when applied thereto.

SUMMARY OF THE INVENTION

The present invention provides methods and compositions that use the combination of Tris and EDTA to inhibit the growth of microorganisms at the site of a wound or burn, and/or to promote the healing of a wound or burn, and/or to reduce the sensation of pain at the site of a wound or burn. The amount of Tris and EDTA applied to a wound or burn can be selected to achieve one or more of the foregoing effects. The Tris and EDTA may be combined with other antimicrobial compositions, such as a detergent or another antimicrobial agent (e.g., aminoglycoside or β-lactam antibiotics), to inhibit growth of microorganisms in or on a living body.

Accordingly, in one aspect the present invention provides methods for inhibiting the growth of microorganisms in, or on, living tissue. The methods of this aspect of the invention include the step of contacting living tissue that is infected with microorganisms with a composition that includes Tris, EDTA, and a detergent, wherein the Tris, EDTA and detergent are present in the composition in amounts sufficient to inhibit growth of the microorganisms.

In another aspect, the present invention provides methods for inhibiting the growth of microorganisms in or on living tissue. The methods of this aspect of the invention include the step of contacting living tissue with a composition comprising Tris and EDTA, wherein the Tris and EDTA are present in amounts that (a) produce a pH of the composition of from 6.0 to 9.0, and (b) inhibit the growth of microorganisms in or on the living tissue.

In a further aspect, the present invention provides methods for promoting the healing of a burn on an animal body. The methods of this aspect of the invention include the step of contacting a burn with a composition comprising Tris and EDTA, wherein the Tris and EDTA are present in amounts effective to promote healing of the burn.

In a further aspect, the present invention provides wound dressings that include from 10 mM Tris to 250 mM Tris and from 1 mM EDTA to 250 mM EDTA. The wound dressings can be applied to wounds to promote wound healing and/or to inhibit the growth of microorganisms in and/or on the wound.

In a further aspect, the present invention provides liquid compositions that include Tris, EDTA, and a pharmaceutically acceptable carrier, wherein the Tris is present at a concentration in the range of from 10 mM to 250 mM, and the EDTA is present at a concentration in the range of from 1 mM to 250 mM.

In a further aspect, the present invention provides methods for promoting the healing of a wound in, or on, a living animal body. The methods of this aspect of the invention include the step of contacting the wound with a composition comprising Tris and EDTA, wherein the Tris and EDTA are present in amounts effective to promote healing of the wound.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
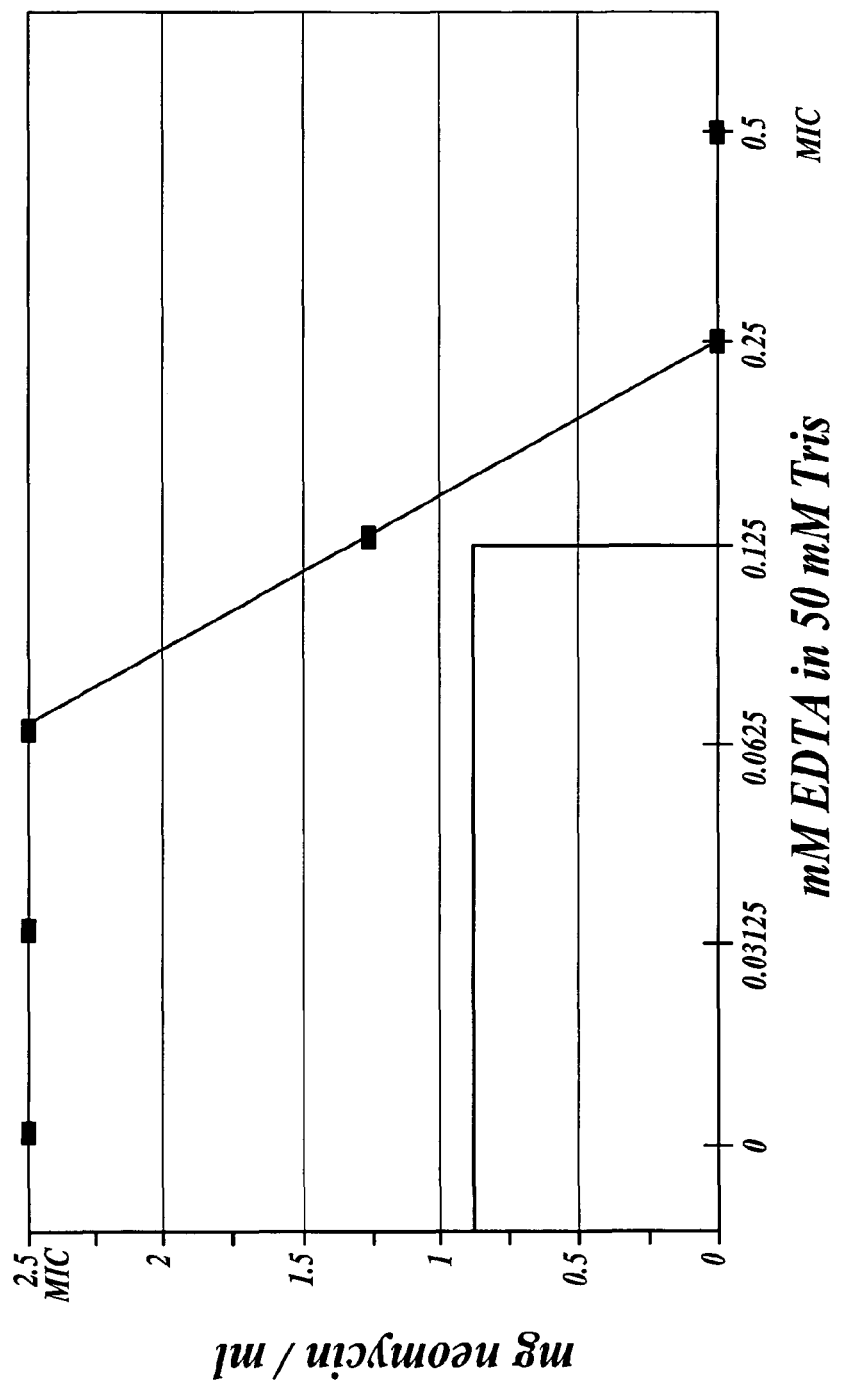
FIG. 1 shows an isobologram illustrating the combined effect of EDTA and neomycin (in 50 mM Tris) on *Staphylococcus aureus*.

As used herein, the phrase "inhibiting the growth of microorganisms" encompasses slowing the rate of growth of a population of microorganisms, and/or completely stopping growth of a population of microorganisms, and/or killing microorganisms.

The abbreviation "EDTA" is an abbreviation for ethylenediaminetetraacetate, the corresponding acid ethylenediaminetetraacetic acid, and salts thereof.

The abbreviation "Tris" is an abbreviation for tris [hydroxymethyl]aminomethane, and pharmaceutically acceptable salts thereof (e.g., Tris-HCL).

As used herein, the term "wound" encompasses physical injuries to living tissue and/or interruption to the integrity of living tissue, such as cuts, tears, abrasions, and lesions and crushed tissue, as well as pimples, ulcers and hemorrhoids.

The term "wound dressing" refers to a material that is used to cover a wound. Examples of wound dressings include ointments, gels, salves, bandages and gauze.

The term "infection," and grammatical equivalents thereof, refers to the state produced by the establishment of an infective agent in or on a suitable host.

The methods of the invention are applicable to any living organism, including mammals, birds, reptiles, amphibians and fish. Examples of mammals that can be treated using the methods of the invention include human beings and domesticated mammals (e.g., dogs, cats, cows, pigs, goats, sheep and horses).

First Aspect of the Invention

In a first aspect, the present invention provides methods for inhibiting the growth of microorganisms in, or on, living tissue. The methods of this aspect of the invention each include the step of contacting living tissue that is infected with microorganisms with a composition including Tris, EDTA, and a detergent, wherein the Tris, EDTA, and detergent are present in the composition in amounts sufficient to inhibit growth of the microorganisms. The composition that includes Tris, EDTA, and a detergent can be, for example, a liquid solution including Tris, EDTA, and a detergent, or, for example, a gel, cream or ointment. By way of example, a wound can be washed with a solution containing Tris, EDTA, and a detergent, and then a composition containing an antimicrobial agent can be applied to the wound. Typically, the composition containing the antimicrobial agent does not include a detergent.

Examples of bacterial genera and species that are inhibited by the methods of the present invention include: *Aerobacter* spp.; *Aeromonas* spp.; *Bacillus* spp.; *Bordetella* spp; *Campylobacter* spp.; *Chlamydia* spp.; *Corynebacterium* spp.; *Escherichia* spp., such as *Escherichia coli*; *Helicobacter pylori*; *Klebsiella pneumoniae*; *Legionella pneumophiia*; *Leptospira* spp.; *Mycobacterium* spp.; *Neisseria* spp.; *Nocardia* spp.; *Proteus* spp.; *Pseudomonas aeruginosa*; *Rhodococcus equi*, *Salmonella* spp.; *Shigella* spp.; *Staphylococcus* spp.; *Streptococcus* spp.; *Vibrio* spp.; *Yersinia* spp.; *Actinomycetes* spp.; *Propionibacterium* spp.; and *Streptomyces* spp.

Examples of fungal genera and species that are inhibited by the methods of the present invention include: *Aspergillus* spp., *Fusarium* spp., *Mucor* spp., *Penicillium* spp., *Trichophyton* spp., *Microsporum* spp., *Candida* spp., *Malessizia* spp., *Psuedallescheria* spp., *Paecilomyces* spp., *Scedosporium* spp and *Dematiaceous fungi*.

A variety of living tissues of an animal body can be treated using the methods of this aspect of the present invention. For example, the methods of this aspect of the present invention can be used to inhibit the growth of microorganisms on skin lesions, burns on the skin, or on wounds (such as cuts or abrasions) of the skin. The methods of this aspect of the present invention can also be used, for example, to inhibit the growth of microorganisms within an animal body. For example, the methods of this aspect of the present invention can be used to inhibit the growth of microorganisms within a body cavity (e.g., abdomen) or a joint (e.g., a knee joint). The methods of this aspect of the present invention can also be used, for example, to inhibit the growth of microorganisms on the surface of an eye. The methods of this aspect of the present invention can also be used, for example, to inhibit the growth of microorganisms in the mouth (e.g., by lavaging or swabbing a portion of the mouth with a composition comprising Tris, EDTA, and a detergent, or, for example, by gargling with a composition comprising Tris, EDTA, and a detergent). For inhibiting the growth of microorganisms within an animal body, the methods of the present invention typically use a composition comprising Tris, EDTA, and a detergent wherein the detergent is used at a concentration of less than 1% (by weight).

In the practice of the methods of this aspect of the present invention, the living tissue can be contacted with the composition comprising Tris, EDTA, and a detergent by any useful means. For example, the composition can be poured or sprayed onto tissue on a surface of a living organism, or can be injected into a living organism (e.g., injected into an infected joint), or can be soaked into a wound dressing and the dressing applied to a wound or site of infection for a period of time sufficient to clean the wound or site of infection, or can be introduced onto the surface of an eye, or into the ear canal, using a dropper. Ointments, creams or gels comprising Tris, EDTA, and a detergent may, for example, be rubbed onto a surface of a living organism. Other examples of methods for contacting living tissue with a composition comprising Tris, EDTA, and a detergent include flushing or irrigating the living tissue with a solution containing Tris, EDTA, and a detergent; rubbing living tissue with a medical dressing containing a solution containing Tris, EDTA, and a detergent (e.g., to clean and disinfect a wound and surrounding tissue); spraying living tissue (e.g., by using a nebulizer) with a solution containing Tris, EDTA and a detergent; introducing a solution containing Tris, EDTA and a detergent into a living body using, for example, a tube, catheter, canula or endoscopic device; introducing a solution containing Tris, EDTA and a detergent into an orifice of a living body using, for example, a suppository or tampon; and contacting oral tissue with a solution containing Tris, EDTA and a detergent, for example by gargling or rinsing the oral cavity with a solution containing Tris, EDTA and a detergent.

Wound dressings suitable for use in the methods of the present invention for contacting a wound, or site of infection, with a composition comprising Tris, EDTA, and a detergent can be any material that is biologically acceptable and suitable for placing on a wound. In exemplary embodiments, the wound dressing may be a woven or non-woven fabric of synthetic or nonsynthetic fibers, or any combination thereof. For example, the wound dressing can be gauze. The gauze may be absorbent and can be, for example, wetted with a composition including Tris, EDTA and a detergent. The dressing may also comprise a support, such as a polymer foam, a natural or man-made sponge, a gel or a membrane that may absorb or have disposed thereon, a composition comprising Tris, EDTA, and a detergent. An example of a useful gel is KY™ gel (sodium carboxymethylcellulose 711 4F (Hercules, Inc., Wilmington, Del.)) Again by way of example, the support can be a film, a natural or synthetic polymer, or a rigid or malleable material.

Examples of concentrations of Tris in the compositions used in the practice of this aspect of the invention are in the range of from 10 mM to 250 mM, such as from 10 mM to 80 mM, or such as from 10 mM to 50 mM (e.g., 20 mM).

Examples of concentrations of EDTA in the compositions used in the practice of this aspect of the invention are in the range of from 1 mM to 250 mM, or such as from 1 mM to 50 mM, such as from 1 mM to 20 mM (e.g., 8 mM).

Examples of concentrations of detergent in the compositions used in the practice of this aspect of the invention are in the range of from 1% to 30%, such as from 1% to 20%, or such as from 1% to 10%, wherein the percentage values are volume/volume percentages.

Examples of detergents that are useful in the practice of the present invention include anionic detergents, cationic detergents, amphoteric detergents, and nonionic detergents. Specific examples of useful detergents include cocamidopropyl betaine, cocamphodiacetate, sodium, lauryl sulfate, sodium alkyl ether sulfate, lauramide DEA, and sodium $C_{14}$-$C_{16}$ olefin sulfonate.

Compositions used in the practice of the methods of the present invention can optionally include an additional antimicrobial agent. The additional antimicrobial agent inhibits the growth of microorganisms, such as bacteria and fungi.

Examples of useful antimicrobial agents include: β-lactams (penicillins and cephalosporins), vancomycins, bacitracins, macrolides (erythromycins), lincosamides (clindomycin), chloramphenicols, tetracyclines, aminoglycosides (gentamicins), amphotericins, cefazolins, clindamycins, mupirocins, sulfonamides and trimethoprim, rifampicins, metronidazoles, quinolones, novobiocins, polymixins and Gramicidins, and any salts or variants thereof. Tetracyclines include, but are not limited to, immunocycline, chlortetracycline, oxytetracycline, demeclocycline, methacycline, doxycycline and minocycline. Aminoglycoside antibiotics include, but are not limited to, gentamicin, amikacin and neomycin. Colloidal silver, or a solution of silver, may also be used as an additional antimicrobial agent. Typically, when silver is used as an antibiotic in the presence of Tris, the amount of Tris used is higher than if the silver was not present (e.g., 30 mM Tris instead of 20 mM Tris). A combination of two, or more, additional antibiotics may be used, for example to inhibit the growth of microorganisms that are completely, or partially, resistant to a single antibiotic.

Effective dosages of art-recognized antimicrobial agents are know to those of ordinary skill in the art, and are disclosed, for example, in the *Compendium of Veterinary Products*, Bayer Healthcare LLC, 7$^{th}$ edition and in the *Physician's Desk Reference*, 59th edition, 2005. Exemplary useful concentration ranges for colloidal silver are from 1 ppm to 300 ppm, such as from 1 ppm to 50 ppm, or such as from 1 ppm to 30 ppm.

Additionally, a pharmaceutically acceptable carrier can be included in the compositions useful in the practice of the methods of the first aspect of the invention. The term "pharmaceutically acceptable carrier" as used herein refers to any pharmaceutically acceptable solvent of Tris, EDTA and a detergent that allows a composition comprising Tris, EDTA and a detergent to be administered to living tissue. The detergent does not have to dissolve in the pharmaceutically acceptable carrier, but may disperse therein. A "pharmaceutically acceptable carrier" as used herein, therefore, refers to such solvents as, but not limited to, water, saline, physiological saline, ointments, creams, oil-water emulsions, gels, or any other solvent or combination of solvents and compounds known to one of skill in the art that is pharmaceutically and physiologically acceptable to a human or animal.

Other components can be included in the compositions used in the practice of this aspect of the invention. For example, vitamins can be included in the compositions, such as vitamin E. Exemplary useful concentration ranges for vitamin E are from 100 IU/ml to 500 IU/ml, such as from 200 IU/ml to 400 IU/ml, or such as from 20 IU/ml to 500 IU/ml. Again, by way of example, an anti-inflammatory agent (e.g., a steroidal or non-steroidal antiinflammatory agent) can be included in the compositions used in this aspect of the invention. Effective dosages of anti-inflammatory agents are disclosed, for example, in *The Compendium of Veterinary Products*, Bayer Healthcare LLC, 7$^{th}$ edition, and in the *Physician's Desk Reference*, 59th edition, 2005.

Other examples of components that can be included in the compositions used in the practice of this aspect of the invention include: Lecithin (e.g., at a concentration of from 2% (v/v) to 50% (v/v)); Glycerin (e.g., at a concentration of from 1% (v/v) to 50% (v/v)); Pluronic F-127 (e.g., at a concentration of from 5% (v/v) to 50% (v/v)); Methyl Paraben (e.g., at a concentration of from 0.1% (v/v) to 10% (v/v)); aloe vera, polypropylene glycol ethoxylate, and/or polaxamer 407.

Second Aspect of the Invention

In a second aspect, the present invention provides methods for inhibiting the growth of microorganisms in, or on, living tissue, wherein the methods of this aspect of the invention each include the step of contacting living tissue with a composition (e.g., an aqueous composition) comprising Tris and EDTA, wherein the Tris and EDTA are present in amounts that (a) produce a pH of the composition of from 6.0 to 9.0, and (b) inhibit the growth of microorganisms in, or on, the living tissue. The living tissue may be infected with microorganisms. Thus, the methods of this aspect of the invention can be used, for example, to inhibit the growth of microorganisms in, or on, living tissue that is infected with microorganisms, or can be used, for example, as a prophylactic treatment to prevent the growth of microorganisms in, or on, living tissue that is not yet infected with microorganisms.

By way of example, living tissue can be washed with a solution containing Tris, EDTA and a detergent, wherein the Tris and EDTA are present in amounts that (a) produce a pH of the composition of from 6.0 to 9.0, and (b) inhibit the growth of microorganisms in, or on, the living tissue, and then a composition containing an antimicrobial agent can be applied to the wound. Typically, the composition containing the antimicrobial agent does not include a detergent.

In some embodiments of this aspect of the invention Tris and EDTA are present in the composition in amounts that produce a pH of the composition of from 6.5 to 8.5. In some embodiments of this aspect of the invention Tris and EDTA are present in the composition in amounts that produce a pH of the composition of from 7.0 to 8.5. It is a feature of the methods of this aspect of the invention that the Tris and EDTA are present in the composition in amounts that are sufficient to produce a pH within the range of from 6.0 to 9.0, without requiring the addition of a pH adjusting agent (e.g., an acid, such as hydrochloric acid, or a base, such as sodium hydroxide) to adjust the pH of the composition to a value within the range of from 6.0 to 9.0.

Amounts of Tris and EDTA that produce a pH of the composition of from 6.0 to 9.0 can be empirically determined. For example, Tris (e.g., Tris powder, or a solution of Tris) can be added to a solution of EDTA, having a desired concentration, until a desired pH is achieved (pH can be continuously or periodically monitored using a pH meter). Again by way of example, EDTA (e.g., EDTA powder, or a solution of EDTA) can be added to a solution of Tris, having a desired concentration, until a desired pH is achieved. By way of further example, powdered Tris and EDTA can be dissolved together, or sequentially, until the desired pH of the solution of Tris and EDTA is obtained. Typically it is desirable to maximize the amount of EDTA in the solution of Tris and EDTA, because EDTA is usually a more potent antimicrobial agent than Tris, and EDTA is also less expensive than Tris.

A list of exemplary microbial species is provided, supra, in connection with the first aspect of the invention. The growth of these exemplary microbial species is inhibited by the methods of the first aspect of the present invention, and also by the methods of the second aspect of the present invention.

Any living tissue of an animal body can be treated using the methods of this aspect of the present invention. The description of the methods of the first aspect of the present invention provides examples of uses of the methods of the first aspect of the present invention. The methods of the second aspect of the present invention are also applicable to these exemplary uses.

One or more detergents may also be included in the compositions useful in the second aspect of the invention. A list of exemplary detergents (and useful concentration ranges for these detergents) is provided, supra, in connection with the first aspect of the invention. These detergents (and the disclosed concentration ranges) are also useful in the compositions used in the practice of the second aspect of the present invention.

In the practice of the methods of this aspect of the present invention, the living tissue can be contacted with the composition comprising Tris and EDTA by any useful means. Examples of methods that can be used to contact living tissue with a composition comprising Tris, EDTA and a detergent are provided, supra, in the description of the first aspect of the present invention. These exemplary methods are also useful, in the practice of the second aspect of the present invention, for contacting living tissue with a composition comprising Tris and EDTA. By way of further example, a composition that includes Tris and EDTA can be introduced into human lungs using an inhaler, or other device adapted to deliver a composition to the lungs of a subject in need thereof. Examples of useful devices for delivering a composition that includes Tris and EDTA into human lungs includes the Pari® LC PLUS jet nebulizer (Pari Respiratory Equipment, Inc., Richmond, Va.), and the delivery systems disclosed in U.S. Pat. Nos. 5,458,135; 5,740,794; 5,775,320; and 5,785,049. Examples of dry powder inhalers suitable for use in the practice of the present invention are disclosed in U.S. Pat. Nos. 5,740,794, 5,785,049, 5,673,686, and 4,995,385.

The compositions used in the practice of the methods of the second aspect of the present invention can optionally include an additional antimicrobial agent. The additional antimicrobial agent kills, or inhibits the growth and/or division, of microorganisms including bacteria and fungi. Examples of useful antimicrobial agents are set forth in the description of the first aspect of the present invention. These antimicrobial agents (and the disclosed concentration ranges) are also useful in the compositions used in the practice of the second aspect of the present invention.

Additionally, a pharmaceutically acceptable carrier may be included in the compositions useful in the second aspect of the invention. Examples of useful pharmaceutically acceptable carriers are set forth in the description of the first aspect of the present invention. These pharmaceutically acceptable carriers can also be included in the compositions used in the practice of the second aspect of the present invention.

Other components can be included in the compositions used in the practice of this aspect of the invention. For example, vitamins can be included in the compositions, such as vitamin E. Again, by way of example, an anti-inflammatory agent can be included in the compositions used in this aspect of the invention. Examples of useful vitamins and anti-inflammatory agents are set forth in the description of the first aspect of the present invention.

Third Aspect of the Invention

In a third aspect, the present invention provides methods for promoting the healing of a burn on an animal body. The methods of this aspect of the invention each include the step of contacting a burn with a composition comprising Tris and EDTA, wherein the Tris and EDTA are present in amounts effective to promote healing of the burn.

The methods of the present invention promote the healing of a burn, that is, they accelerate the rate of healing of the burn, and/or otherwise create the conditions at the site of the burn that favor healing of the burn.

The term "burn" as used herein refers to tissue injury caused by thermal, chemical, or radiation exposure or abrasive friction to the skin. A burn may be a "first-degree burn" with superficial damage to the outer cornified layer, a "second-degree burn" with damage extending down into the epidermal layer of cells but is not of sufficient extent that regeneration of the skin is prevented, or a "third-degree burn" where the injury extends below the dermis to the underlying tissue and wherein repair of the skin is not possible without grafting.

An example of a concentration range for the amount of Tris used in the compositions used in the practice of the third aspect of the invention is from 10 mM to 250 mM, such as from 10 mM to 80 mM, such as from 10 mM to 50 mM (e.g., 20 mM).

An example of a concentration range for the amount of EDTA used in the compositions used in the practice of the third aspect of the invention is from 1 mM to 250 mM, or such as from 1 mM to 50 mM, such as from 1 mM to 20 mM (e.g., 8 mM).

One or more detergents may also be included in the compositions useful in the third aspect of the invention. A list of exemplary detergents (and useful concentration ranges for these detergents) is provided, supra, in connection with the first aspect of the invention. These detergents (and the disclosed concentration ranges) are also useful in the compositions used in the practice of the third aspect of the present invention. Preferred detergents cause little or no irritation of the burn when used in the concentrations described herein.

In the practice of the methods of this aspect of the present invention, a burn can be contacted with the composition comprising Tris and EDTA by any useful means. Examples of methods that can be used to contact a burn with a composition comprising Tris and EDTA are provided, supra, in the description of the first aspect of the present invention and in the description of the second aspect of the present invention. These exemplary methods are also useful, in the practice of the third aspect of the present invention, for contacting a burn with a composition comprising Tris and EDTA.

The compositions used in the practice of the methods of the third aspect of the present invention can optionally include an additional antimicrobial agent. The additional antimicrobial agent kills, or inhibits the growth and/or division, of microorganisms including bacteria and fungi. Examples of useful antimicrobial agents are set forth in the description of the first aspect of the present invention. These antimicrobial agents (and the disclosed concentration ranges) are also useful in the compositions used in the practice of the third aspect of the present invention.

Additionally, a pharmaceutically acceptable carrier may be included in the compositions useful in the third aspect of the invention. Examples of useful pharmaceutically acceptable carriers are set forth in the description of the first aspect of the present invention. These pharmaceutically acceptable carriers can also be included in the compositions used in the practice of the third aspect of the present invention.

Other components can be included in the compositions used in the practice of this aspect of the invention. For example, vitamins can be included in the compositions, such as vitamin E. Again, by way of example, an anti-inflammatory agent can be included in the compositions used in this aspect of the invention. Examples of useful vitamins and anti-inflammatory agents are set forth in the description of the first aspect of the present invention.

In some embodiments of this aspect of the invention, Tris and EDTA are present in the composition in amounts that produce a pH of the composition of from 6.5 to 8.5. In some embodiments of this aspect of the invention, Tris and EDTA are present in the composition in amounts that produce a pH of the composition of from 7.0 to 8.5. It is a feature of the methods of this aspect of the invention, that the Tris and EDTA are present in the composition in amounts that are sufficient to produce a pH within the range of from 6.0 to 9.0, without requiring the addition of a pH adjusting agent (e.g., an acid, such as hydrochloric acid, or a base, such as sodium hydroxide) to adjust the pH of the composition to a value within the range of from 6.0 to 9.0. An advantage of these embodiments of this aspect of the invention is that a potentially caustic or irritating agent (e.g., hydrochloric acid or sodium hydroxide) does not have to be added to the composition, thereby reducing the chance that the composition will irritate the burn.

A representative method for determining concentrations of Tris and EDTA that produce a desired pH, without the addition of a further pH adjusting agent, is described in connection with the methods of the second aspect of the invention.

Fourth Aspect of the Invention

In a fourth aspect, the present invention provides wound dressings that each include Tris and EDTA. In some embodiments, the wound dressings include from 10 mM Tris to 250 mM Tris (e.g., from 10 mM Tris to 80 mM Tris, or, for example, from 10 mM Tris to 50 mM Tris), and from 1 mM EDTA to 250 mM EDTA (e.g., from 1 mM EDTA to 50 mM EDTA, or, for example, from 1 mM EDTA to 20 mM EDTA).

The Tris and EDTA may be applied to a wound dressing as a solution of Tris and EDTA and allowed to dry on the dressing. In these embodiments, liquid from a wound dissolves the dried Tris and EDTA when the dressing is applied to a wound.

Wound dressings can be made, for example, from any material that is biologically acceptable and suitable for placing on a wound. In exemplary embodiments, the wound dressing may be made from a woven or non-woven fabric of synthetic or non-synthetic fibers, or any combination thereof. The dressing may also include a support, such as a polymer foam, a natural or man-made sponge, a gel or a membrane that may absorb or have disposed thereon, a composition comprising Tris and EDTA. An example of a useful gel is KY™ gel (sodium carboxymethylcellulose 711 4F, available from Hercules, Inc., Wilmington, Del.) Again by way of example, the support can be a film, a natural or synthetic polymer, or a rigid or malleable material (e.g., gauze). The wound dressing may be absorbent and can be, for example, wetted with an antimicrobial composition of the present invention before applying the gauze to an infected wound or other site.

The present invention also contemplates that a wound dressing, or portion thereof, may be impregnated with a composition including Tris and EDTA, and then dried. This allows the impregnated dressing to be stored for later use, or to avoid excessively dampening an injured area. The composition, including Tris and EDTA, may be applied to a surface of the dressing by wetting the surface with a solution of the composition and drying the dressing to deposit the composition thereon. A concentration of the composition, including Tris and EDTA, that is effective for promoting wound repair, and/or inhibiting the growth of microorganisms, may be attained when the dressing is wetted by the patient's body.

An additional antimicrobial agent can also be included in the wound dressings. The additional antimicrobial agent kills, or inhibits the growth and/or division, of microorganisms including bacteria and fungi. Examples of useful antimicrobial agents are set forth in the description of the first aspect of the present invention. These antimicrobial agents (and the disclosed concentration ranges) can also be included in the wound dressings of the fourth aspect of the present invention.

Additionally, a pharmaceutically acceptable carrier may be included in the wound dressings of the fourth aspect of the invention. Examples of useful pharmaceutically acceptable carriers are set forth in the description of the first aspect of the present invention. These pharmaceutically acceptable carriers can also be included in the wound dressings of the fourth aspect of the present invention.

Other components can be included in the compositions used in the practice of this aspect of the invention. For example, vitamins can be included in the compositions, such as vitamin E. Exemplary useful concentration ranges for vitamin E are from 100 IU/ml to 500 IU/ml, such as from 200 IU/ml to 400 IU/ml, or such as from 20 IU/ml to 500 IU/ml. Again, by way of example, an anti-inflammatory agent (e.g., a steroidal or non-steroidal antiinflammatory agent) can be included in the compositions used in this aspect of the invention. Effective dosages of anti-inflammatory agents are disclosed, for example, in the *Compendium of Veterinary Products*, Bayer Healthcare LLC, $7^{th}$ edition, and in the *Physician's Desk Reference*, 59th edition, 2005.

In some embodiments of the fourth aspect of the invention, Tris and EDTA are present in the wound dressings in amounts that produce a pH of from 6.0 to 9.0 when the wound dressing is applied to a wound. In some embodiments of the fourth aspect of the invention, Tris and EDTA are present in the wound dressings in amounts that produce a pH of from 6.5 to 8.5 when the wound dressing is applied to a wound. In some embodiments of the fourth aspect of the invention, Tris and EDTA are present in the wound dressings in amounts that produce a pH of from 7.0 to 8.5 when the wound dressing is applied to a wound. It is a feature of these embodiments of this aspect of the invention that the Tris and EDTA are present in a wound dressing in amounts that are sufficient to produce a pH within the range of from 6.0 to 9.0, without requiring the addition of a pH adjusting agent (e.g., an acid, such as hydrochloric acid, or a base, such as sodium hydroxide) to adjust the pH to a desired value. An advantage of these embodiments of this aspect of the invention is that a potentially caustic or irritating agent (e.g., hydrochloric acid or sodium hydroxide) does not have to be included in the wound dressing, thereby reducing the chance that the wound dressing will irritate a wound.

A representative method for determining concentrations of Tris and EDTA that produce a desired pH, without the addition of a further pH adjusting agent, is described in connection with the methods of the second aspect of the invention.

Fifth Aspect of the Invention

In a fifth aspect, the present invention provides a liquid composition that includes Tris, EDTA, and a pharmaceutically acceptable carrier, wherein the Tris is present in the liquid composition at a concentration in the range of from 10 mM to 250 mM (e.g., from 10 mM Tris to 80 mM Tris, or, for example, from 10 mM Tris to 50 mM Tris) and the EDTA is present in the liquid composition at a concentration in the range of from 1 mM to 250 mM (e.g., from 1 mM EDTA to 50 mM EDTA, or, for example, from 1 mM EDTA to 20 mM EDTA).

In the context of the fifth aspect of the present invention, the term "liquid composition" includes, for example, solutions, ointments, lotions, gels, and creams.

In the context of the fifth aspect of the present invention, the term "pharmaceutically acceptable carrier" refers to any pharmaceutically acceptable solvent of Tris and EDTA that allows a liquid composition of the fifth aspect of the invention to be administered to living tissue. A "pharmaceutically acceptable carrier" as used herein, therefore, refers to such solvents as, but not limited to saline, physiological saline, ointments, creams, oil-water emulsions, gels (such as hydrogels), or any other solvent or combination of solvents and compounds known to one of skill in the art that is pharmaceutically and physiologically acceptable to the recipient human or animal. In the context of the fifth aspect of the present invention, the term "pharmaceutically acceptable carrier" does not include water by itself.

One or more detergents may also be included in the liquid compositions of the fifth aspect of the invention. A list of exemplary detergents (and useful concentration ranges for these detergents) is provided, supra, in connection with the first aspect of the invention. These detergents (and the disclosed concentration ranges) can also be included in the compositions of the fifth aspect of the present invention.

The liquid compositions of the fifth aspect of the present invention can optionally include an additional antimicrobial agent. The additional antimicrobial agent kills, or inhibits the growth and/or division, of microorganisms including bacteria and fungi. Examples of useful antimicrobial agents are set forth in the description of the first aspect of the present invention. These antimicrobial agents (and the disclosed concentration ranges) can be included in the liquid compositions of the fifth aspect of the present invention.

Other components can be included in the compositions of this aspect of the invention. For example, vitamins can be included in the compositions, such as vitamin E. Exemplary useful concentration ranges for vitamin E are from 100 IU/ml to 500 IU/ml, such as from 200 IU/ml to 400 IU/ml, or such as from 20 IU/ml to 500 IU/ml. Again, by way of example, an anti-inflammatory agent (e.g., a steroidal or non-steroidal antiinflammatory agent) can be included in the compositions used in this aspect of the invention. Effective dosages of anti-inflammatory agents are disclosed, for example, in the *Compendium of Veterinary Products*, Bayer Healthcare LLC, $7^{th}$ edition, and in the *Physician's Desk Reference*, 59th edition, 2005.

In some embodiments of the fifth aspect of the invention, Tris and EDTA are present in the liquid compositions in amounts that produce a pH of from 6.0 to 9.0. In some embodiments of the fifth aspect of the invention, Tris and EDTA are present in the liquid compositions in amounts that produce a pH of from 6.5 to 8.5. In some embodiments of the fifth aspect of the invention, Tris and EDTA are present in the liquid compositions in amounts that produce a pH of from 7.0 to 8.5. It is a feature of these embodiments of this aspect of the invention that the Tris and EDTA are present in the liquid compositions in amounts that are sufficient to produce a pH within the range of from 6.0 to 9.0, without requiring the addition of a pH adjusting agent (e.g., an acid, such as hydrochloric acid, or a base, such as sodium hydroxide) to adjust the pH to a desired value. An advantage of these embodiments of this aspect of the invention is that a potentially caustic or irritating agent (e.g., hydrochloric acid or sodium hydroxide) does not have to be included in the compositions, thereby reducing the chance that the compositions will irritate a wound or other tissue.

A representative method for determining concentrations of Tris and EDTA that produce a desired pH, without the addition of a further pH adjusting agent, is described in connection with the methods of the second aspect of the invention.

Sixth Aspect of the Invention

In a sixth aspect, the present invention provides methods for promoting the healing of a wound in, or on, a mammalian body. The methods of this aspect of the invention each include the step of contacting the wound with a composition comprising Tris and EDTA, wherein the Tris and EDTA are present in amounts effective to promote healing of the wound. The ability of the compositions used in this aspect of the invention to promote wound healing is in addition to the ability of the compositions to inhibit the growth of microorganisms.

Examples of concentrations of Tris in the compositions used in the practice of this aspect of the invention are in the range of from 10 mM to 250 mM, such as from 10 mM to 80 mM, or such as from 10 mM to 50 mM (e.g., 20 mM).

Examples of concentrations of EDTA in the compositions used in the practice of this aspect of the invention are in the range of from 1 mM to 250 mM, or such as from 1 mM to 50 mM, such as from 1 mM to 20 mM (e.g., 8 mM).

One or more detergents may also be included in the compositions useful in the sixth aspect of the invention. A list of exemplary detergents (and useful concentration ranges for these detergents) is provided, supra, in connection with the first aspect of the invention. These detergents (and the disclosed concentration ranges) are also useful in the compositions used in the practice of the sixth aspect of the present invention.

In the practice of the methods of this aspect of the present invention, a wound can be contacted with the composition comprising Tris and EDTA by any useful means (e.g., lavage, rinse). Examples of methods that can be used to contact a wound with a composition comprising Tris and EDTA are provided, supra, in the description of the first aspect of the present invention. These exemplary methods are also useful, in the practice of the sixth aspect of the present invention, for contacting a wound with a composition comprising Tris and EDTA.

The compositions used in the practice of the methods of the sixth aspect of the present invention can optionally include an additional antimicrobial agent and/or antifungal agent. The additional antimicrobial agent and/or antifungal agent kills, or inhibits the growth and/or division, of microorganisms including bacteria and fungi. Examples of useful antimicrobial agents and antifungal agents are set forth in the description of the first aspect of the present invention. These antimicrobial agents and antifungal agents (and the disclosed concentration ranges) are also useful in the compositions used in the practice of the sixth aspect of the present invention.

Additionally, a pharmaceutically acceptable carrier may be included in the compositions useful in the sixth aspect of the invention. Examples of useful pharmaceutically acceptable carriers are set forth in the description of the first aspect of the present invention. These pharmaceutically acceptable carriers can also be included in the compositions used in the practice of the sixth aspect of the present invention.

Other components can be included in the compositions used in the practice of this aspect of the invention. For example, vitamins can be included in the compositions, such as vitamin E. Exemplary useful concentration ranges for vitamin E are from 100 IU/ml to 500 IU/ml, such as from 200 IU/ml to 400 IU/ml, or such as from 20 IU/ml to 500 IU/ml. Again, by way of example, an anti-inflammatory agent (e.g., a steroidal or non-steroidal antiinflammatory agent) can be included in the compositions used in this aspect of the invention. Effective dosages of anti-inflammatory agents are disclosed, for example, in the *Compendium of Veterinary Products*, Bayer Healthcare LLC, $7^{th}$ edition, and in the *Physician's Desk Reference*, 59th edition, 2005.

In some embodiments of the sixth aspect of the invention, Tris and EDTA are present in the composition in amounts that produce a pH of the composition of from 6.0 to 9.0. In some embodiments of the sixth aspect of the invention, Tris and EDTA are present in the composition in amounts that produce a pH of the composition of from 6.5 to 8.5. In some embodiments of the sixth aspect of the invention, Tris and EDTA are present in the composition in amounts that produce a pH of the composition of from 7.0 to 8.5. It is a feature of these embodiments of this aspect of the invention that the Tris and EDTA are present in the composition in amounts that are sufficient to produce a pH within the range of from 6.0 to 9.0, without requiring the addition of a pH adjusting agent (e.g., an acid, such as hydrochloric acid, or a base, such as sodium hydroxide) to adjust the pH of the composition to a desired value.

A representative method for determining concentrations of Tris and EDTA that produce a desired pH, without the addition of a further pH adjusting agent, is described in connection with the methods of the second aspect of the invention.

The following examples merely illustrate the best mode now contemplated for practicing the invention, but should not be construed to limit the invention.

Example 1

Non-Toxicity of the Combination of Tris and EDTA to Fish

An in vivo evaluation of a solution of 5 mM Tris, 50 mM EDTA was conducted on SPF (specific pathogen free) catfish. After a 15 minute immersion time in the Tris-EDTA solution, the catfish showed no ill effects. With a 30 minute incubation period, however, the fish rolled but recovered when removed from the dip. None of the fish exhibited any long-term side effects from the immersion treatment with Tris-EDTA.

Example 2

An Antibiotic-EDTA Composition is Effective in Treating a Microbial Infection of Fish The data show that a bath treatment with EDTA-Tris in conjunction with a number of antibiotics was well tolerated by fish and was effective in healing ulcerated lesions that had not responded to traditional antibiotic therapy, such as an injection of antibiotics or medicated food. An immersion treatment of the infected animals of 5 to 10 minutes on alternate days over a six day period promoted healing of most ulcers.

Ten Koi (*Cyprinus carpio*) obtained from a commercial fish hatchery and suffering from surface ulcers, were treated by immersion in 50 mM Tris and 5 mM EDTA containing the antibiotic neomycin (140 mg/100 ml) for 10 minutes.

All of the treated fish had previously been given injections of Azactam, Baytril, and Amikacin. These antibiotics, when injected directly into the fish, had failed to heal visible ulcers. Culture and sensitivity testing of the microbial population present in the ulcers revealed multiple pathogenic species that were highly resistant to conventional antibiotic treatment. Among the species of bacteria found in the ulcers of the fish were representatives of the genera *Aeromonas, Proteus, Klebsiella, Staphylococcus, Streptococcus, Enterobacter* and *Flavobacterium*.

All fish were housed in a communal "hospital tank" before treatment and moved to an isolation tank after each treatment. The temperature of the bath was adjusted to that of the hospital tank temperature, 24 C, and adequate aeration was supplied to the treatment tank. Eight of the fish had external ulcers of various dimensions. Two of the fish were dropsied.

Fish displayed no signs of stress other than becoming hyperemic, which is typical for Koi when handled. Ulcers appeared less red after the first dip treatment and were significantly diminished after two subsequent dips. One of the dropsied fish died, and a Tancho with an ulcer died two days after therapy was begun. Both of these fish, however, had systemic bacterial infections in addition to external lesions.

Example 3

Determination of Synergistic Actions and the Fractional Inhibitory Concentration of an Antimicrobial Agent-Chelator Composition (FTC) Index This example describes a method for determining the FIC values set forth in Example 4. The antibacterial action of combinations of EDTA-Tris and neomycin was measured by a two-dimensional microtiter checkerboard technique described in Gilman et al., *The Pharmacological Basis of Therapeutics*, Goodman and Gilman, eds. pp. 1085-1086 (Macmillan Publishing Co., New York, 1985); Sabath, L. D., *Antimicrob. Agents and Chem.* pp. 210-217 (1967); and Sparks et al., *Vet. Res. Comm.* 18:241-249 (1994). Each of the foregoing publications are incorporated herein by reference.

Each well of a round-bottomed 96-well microtiter plate was inoculated with 0.05 ml of 2-fold dilutions of neomycin, and of EDTA in 50 mM Tris. Then 0.05 ml of an 18-hour old culture of a test organism, containing 106 colony-forming units (CFU) ml, were added to each well. Controls for the culture and media were included in each plate. Plates were covered and incubated at 37° C. for 18-24 hours.

Results were plotted as isobolograms for the determination of antagonistic, neutral or additive, or synergistic effects. To generate isobolograms, FICs of the two test solutions were plotted individually on the x-axis and y-axis to determine the effect of combining the two test solutions on bacterial growth. A line that curves away from the zero point and the coordinates indicated antagonism. A straight line indicated neutral or additive effects. Lines that curved toward the zero point and the coordinates indicated synergism if there was at least a 4-fold decrease in the MIC of each compound, when used in combination, as compared with the MIC of each test compound alone as described in Gilman et al., *The Pharmacological Basis of Therapeutics*, eds. Goodman and Gilman, pp. 1085-1086 (Macmillan Publishing Co., New York, 1985); Sabath, L. D., *Antimicrob. Agents and Chem.* pp. 210-217 (1967) and incorporated herein by reference in their entireties.

A numerical score or Fractional Inhibitory Concentration (FIC) index was determined. The FIC index is equal to the sum of the values of FIC for the individual drugs:

$$FIC = \frac{MIC \text{ of Drug } A \text{ With Drug } B}{MIC \text{ of Drug } A} + \frac{MIC \text{ of Drug } B \text{ With Drug } A}{MIC \text{ of Drug } B}$$

An FIC index greater than 1.0 indicated an antagonistic interaction, an FIC index of 1.0 indicated addition, and an FIC index of less than or equal to 0.5 indicated synergism between the two test agents.

Example 4

The Antibiotic Resistance Profiles, AMC and MBC Values for Test Strains of Staph. Aureus, Ps. Aeruginosa, and Ent. Faecalis Antibiotic resistance profiles were determined by the disc diffusion method on Muellar-Hinton agar according to the method of the National Committee for Clinical Laboratory Standards, "Performance standards for antimicrobial disk and dilution susceptibility tests for bacteria from animals; approved standard M31-A", National Committee for Clinical Laboratory Standards, Villanova, Pa., Vol. 19, No. 11, 1999, pp 16-25 incorporated herein by reference in its entirety.

Antibiotics tested included ampicillin (AM-10), chloramphenicol (C-30), ciprofloxacin (CIP-5), erythromycin (E-15), kanamycin (K-30), gentamicin (GM-10), methicillin/oxacillin (Ox-1), nalidixic acid (NA-30), neomycin (N-30), streptomycin (S-10), sulfisoxazole (G-.25), tetracycline (Te-30), and vancomycin (Va-30).

The antibiotic resistance profiles are shown in Table 1.

TABLE 1

Antibiotic Resistance Profiles of *Staphylococcus Aureus*, *Pseudomonas Aeruginosa*, and *Enterococcus Faecalis* Isolated From Burn Patients

| | Antimicrobic Agents[A] | | | | | | | | | | | |
|---|---|---|---|---|---|---|---|---|---|---|---|---|
| | Am | C | Cip | E | GM | K | NA | N | Ox | S | G | Te | Va |
| S. aureus | R[B] | I | R | R | S | R | R | R | R | S | S | S | S |
| P. aeruginosa | R | R | I | R | I | R | R | R | R | R | R | R | R |
| E. faecalis | S | R | R | R | R | R | R | R | R | R | R | R | R |

[A]Am = ampicillin; C = chloramphenicol; Cip = ciprofloxacin; E = erythromycin; K = kanamycin; GM = gentamicin; NA = nalidixic acid; N = neomycin; Ox = oxacillin/methicillin; S = streptomycin; G = sulfisoxazole; Te = tetracycline; Va = vancomycin.
[B]R = resistant; I = intermediate; S = sensitive.

The minimal inhibitory concentrations (MICs) and minimal bactericidal concentrations (MBCs) for EDTA-Tris and neomycin were determined by the microtiter-dilution method according to the method of National Committee for Clinical Laboratory Standards, "Performance standards for antimicrobial disk and dilution susceptibility tests for bacteria from animals; approved standard M31-A", National Committee for Clinical Laboratory Standards, Villanova, Pa., Vol. 19, No. 11, 1999, pp. 16-25, incorporated herein by reference in its entirety.

The MICs and MBCs are shown in Table 2.

TABLE 2

Minimal Inhibitory Concentrations (MIC) and Minimal Bactericidal Concentrations (MBC) of Mixtures of EDTA (Mm) and Neomycin (mg/ml) in 50 Mm Tris Reacted With *Staphylococcus Aureus*, *Pseudomonas Aeruginosa*, and *Enterococcus Faecalis*

| | MIC | MBC | EDTA + Neomycin | EDTA + Neomycin |
|---|---|---|---|---|
| S. aureus | 1.0 | 0.39 | 3.9 | 1.56 |
| P. aeruginosa | 0.5 | 0.01 | 2.0 | 0.04 |
| E. faecalis | 15.63 | 1.56 | 62.5 | 6.25 |

The Minimal Bactericidal Concentrations (MBC) values for EDTA and neomycin were decreased by at least 75% for bacterial killing (MBC) in those situations in which synergistic potentiation occurred (*Ps. aeruginosa* and *Ent. faecalis*) as shown in Table 3. A decrease of about 50% was observed with *Staph. aureus*.

TABLE 3

Minimal Bactericidal Concentrations (MBC), of *Staph. Aureus*, *Ps. Aeruginosa*, and *Ent. Faecalis* Reacted With EDTA (Mm) and Neomycin (Mg/Ml) in 50 Mm Tris

| Bacterial Species | | Individually Administered | Co-administered |
|---|---|---|---|
| Staphylococcus aureus | EDTA (mM) Neomycin (mg/ml) | 7.81<br>3.13 | 3.9<br>1.56 |
| Pseudomonas aeruginosa | EDTA (mM) Neomycin (mg/ml) | 250<br>5.0 | 20.0<br>0.04 |
| Enterococcus faecalis | EDTA (mM) Neomycin (mg/ml) | 250<br>25.0 | 62.5<br>6.25 |

Specifically in the case of *Staph. aureus*, the MBC values for EDTA and neomycin when combined were decreased by 50% as compared to the bactericidal effect of each when individually administered.

With *Ps. aeruginosa*, the MBC values for EDTA and neomycin when in combination were decreased 99.2% compared to when EDTA or neomycin were individually administered.

In the case of *Ent. faecalis*, MBC values of EDTA and neomycin were both reduced 75% compared to when EDTA and neomycin were administered individually.

Figure 2:
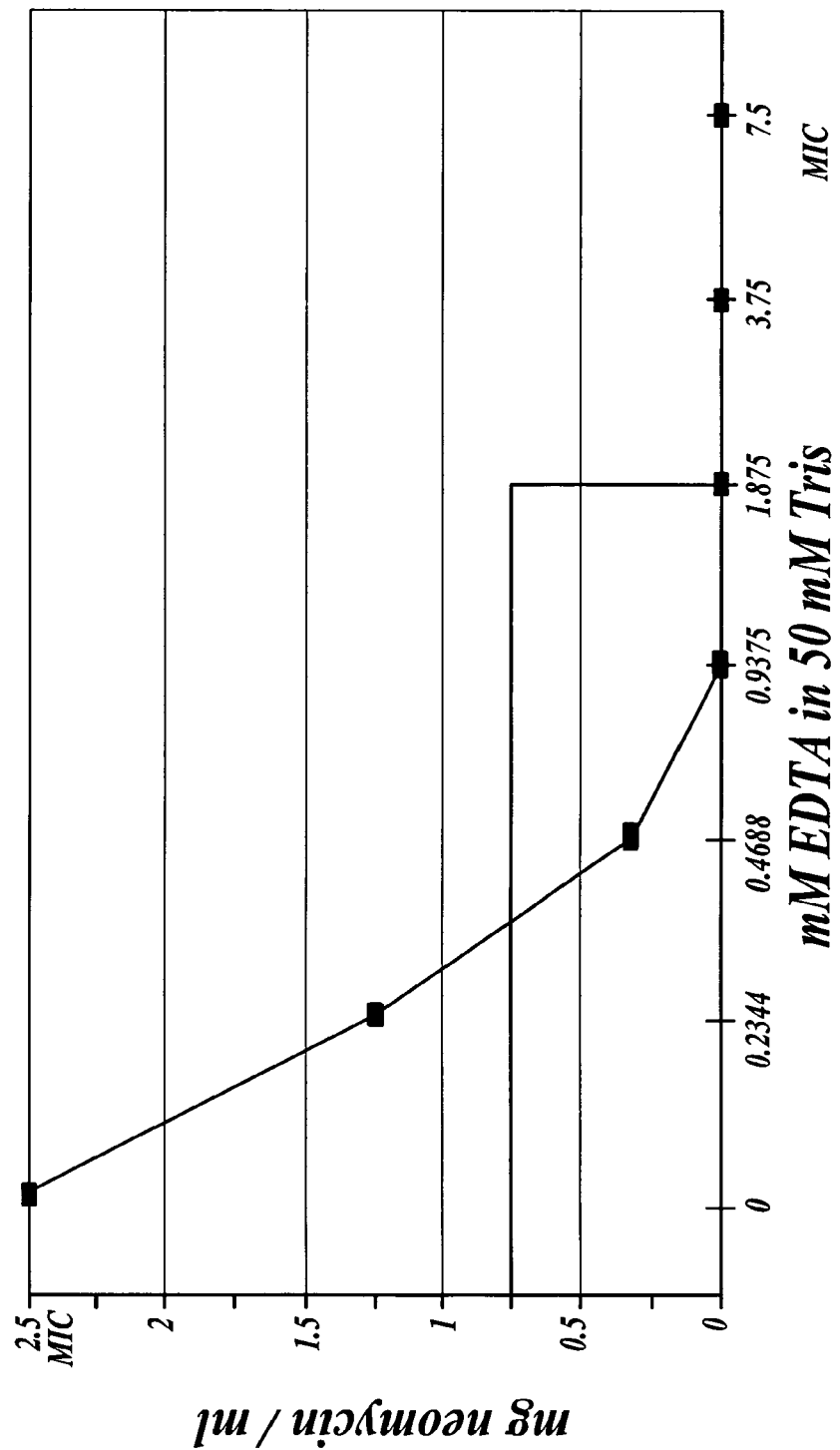
FIG. 2 shows an isobologram illustrating the combined effect of EDTA and neomycin (in 50 mM Tris) on *Pseudomonas aeruginosa*.
Figure 3:
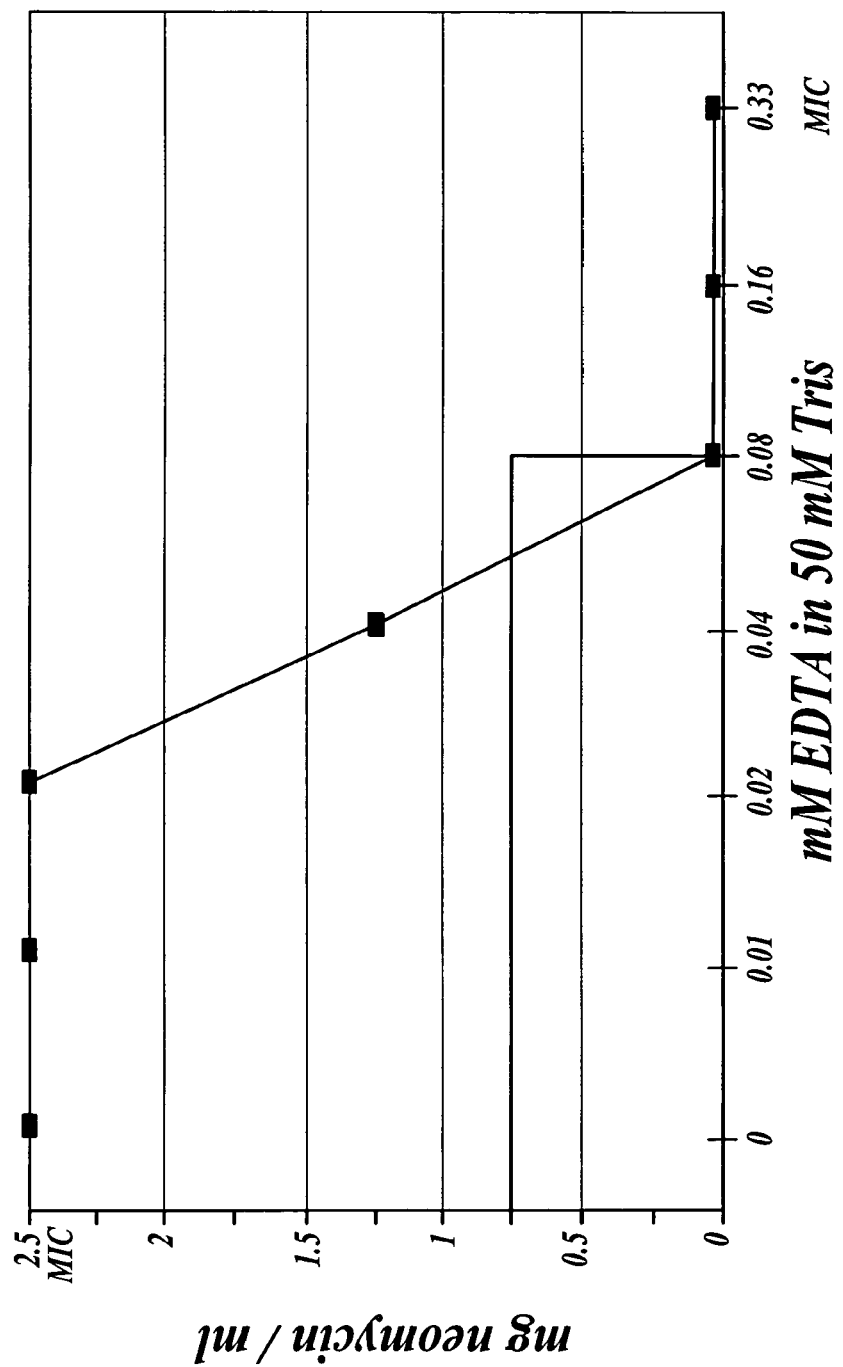
FIG. 3 shows an isobologram illustrating the combined effect of EDTA and neomycin (in 50 mM Tris) on *Enterococcus faecalis*.

Synergistic effects were observed when various concentrations of EDTA-Tris and neomycin were reacted with *Ps. aeruginosa* and *Ent. faecalis*, while an additive effect was observed with *Staph. aureus* as shown in FIGS. 1-3.

Example 5

MIC and FIC Values for Test Species of Aeromonas Spp. Isolated from Fish

The MICs for EDTA and neomycin were determined with three species of *Aeromonas* isolated for ulcerated fish, as shown in Table 4.

TABLE 4

Minimal Inhibitory Concentration (MIC) Data for EDTA in 50 Mm Tris and Neomycin (mg/ml) When Reacted Alone or in Combination Against *Aeromonas Hydrophila*, *Aeromonas Sobri*, and *Aeromonas Caviae*

| Aeromonas sp. | Neomycin | EDTA | Neomycin + EDTA | | FIC |
|---|---|---|---|---|---|
| A. hydrophila | 0.2 | 250 | 0.1 | 62.5 | 0.7 |
| A. sobria | 0.0125 | 15.6 | 0.0075 | 3.88 | 0.31 |
| A. caviae | 0.0125 | <0.49 | 0.00625 | <0.25 | 1.0 |

Example 6

Treatment of Microbially Infected Skin and Oral Lesions

A composition comprising EDTA, Tris and neomycin in KY™ gel carrier was applied to skin ulcers of a turtle, a snake and a frog. Infection was reduced until eliminated, and the treated animals fully healed of their injuries and infections.

A 13 year old domestic short hair cat had developed proliferative gingivitis. The mouth was swabbed with a cotton-tipped swab twice daily for a week with a solution containing 5 mM EDTA, 50 mM Tris, and 2 mg/ml neomycin. After the first week, the mouth and gums were swabbed twice weekly for a further month. Following clearance of the infection from the animal's mouth, there was no recurrence for at least one year. A similar human oral lesion also responded to this treatment. Likewise, mouthwashes also containing EDTA, Tris and neomycin, as above, were used to treat and heal stomatitis of the oral cavities of iguanas and snakes.

Example 7

Animal Inflicted Bite Wound

An animal inflicted bite wound of the human knuckle resulted in a 10 mm×7 mm full thickness flap wound of the skin penetrating the subdermal tissues. It was expected that there would be severe pain and debilitation accompanied by limited use of the affected finger for at least a week. The wound was washed immediately with tap water and coated with emulsion containing 35 mls of hydrous lanolin, 15 mls of 333 IU/ml Vitamin E, and 0.73 gms of EDTA, 0.6 gms of Tris dissolved in 2 mls of distilled water and 0.1 mg/ml of ampicillin. The wound was washed and recoated with emulsion 3 to 4 times per day. A band-aid was used to protect the wound from additional trauma. Minimal to no pain and accelerated healing was observed compared to similar but untreated wounds.

Example 8

Incision Wound

A composition containing 35 mls of hydrous lanolin, 15 mls of 333 UI/ml Vitamin E, and 0.73 gms of EDTA, 0.6 gms of Tris dissolved in 2 mls of distilled water and 0.1 mg/ml of ampicillin was applied once to a small painful cut on a finger. After a single application, the pain was gone along with redness. The lesion healed quickly thereafter. The medication was applied to a 1 day old very painful toe lesion of a sort that is typically sore and red for several days. After 1 application, the pain was gone and the lesion rapidly healed.

Example 9

Open Abscess Wound of Cat

A cat suffering from an abscess, severe necrotizing dermatitis, fascitis, and superficial myositis faced either amputation or euthanasia. The wound was debrided, flushed with sterile saline and 3 gms EDTA, 2.4 gms Tris and 100 mg of ampicillin dissolved in a liter of distilled water. Initially, the wound was dressed with a wet bandage soaked in above solution. The wound was coated with an emulsion of 35 mls of hydrous lanolin, 15 mls of 333 UI/ml Vitamin E, and 0.73 gms of EDTA, 0.6 gms of Tris dissolved in 2 mls of distilled water and 0.1 mg/ml of ampicillin once per day (if a bandage was applied) or 3 to 4 times a day (no bandage was applied). The cat showed no discomfort even when the wound was left open, and a sufficient granulation bed was formed to allow surgical closure in two stages.

Example 10

This example sets forth the formulations of pre-wash solutions.

TABLE 5

|  | Percent Cocamidopropyl Betaine | | | | | |
| --- | --- | --- | --- | --- | --- | --- |
|  | 2.5 | 5 | 10 | 15 | 20 | 25 |
| 0.5M EDTA | 16 µl | 16 µl | 16 µl | 16 µl | 16 µl | 16 µl |
| 1.0 Tris | 20 µl | 20 µl | 20 µl | 20 µl | 20 µl | 20 µl |
| Deionized water | 939 µl | 914 µl | 864 µl | 814 µl | 764 µl | 714 µl |
| Cocamidopropyl betaine | 25 µl | 50 µl | 100 µl | 150 µl | 200 µl | 250 µl |

Total volume = 1.0 ml of prewash.
Final concentrations of EDTA and Tris are 8 mM EDTA and 20 mM Tris.

Example 11

Use of Tris-EDTA-Cocamidopropyl Betaine as an Animal Ear Skin Cleanser

A solution containing cocamidopropyl betaine (5%-15%), 8 mM EDTA and 20 mM Tris, in deionized water, was used by five clinicians to clean the ears of more than 20 dogs. The severity of exudates (ceruminous otitis) varied from mild to severe. The treated external ear canal was filled with warm ear cleanser and gently massaged during a 1-5 minute period. The external ear was then washed with warm saline. The cleaning procedure was repeated as needed to remove all visible exudates and prepare the ear for antimicrobial treatment.

All clinicians reported that the solution was effective, caused minimal to no discomfort (even in severely inflamed ears) and did not worsen the inflammatory process. In addition, the solution was used with no apparent side effects, in several dogs that were subsequently shown to have ruptured tympanic membranes.

Example 12

Tris-EDTA with Cocamidopropyl Betaine as an Antimicrobial Composition

Initially, an 8 mM Tris-20 mM EDTA solution (1x formulation) with 2.5%, 5%, 10%, 15%, 20%, or 25% cocamidopropyl betaine was prepared and compared for cleaning efficacy. The solution containing 10% cocamidopropyl betaine was selected for further testing. The MIC and MBC data for the cocamidopropyl betaine solution, Tris EDTA solution, and Tris-EDTA-cocamidopropyl betaine solution are shown in Tables 6, 7, and 8.

The formulation was tested against *Pseudomonas aeruginosa, Proteus mirabilis, Escherichia coli, Staphylococcus intermedius, Malessezia pachydermatis*, and *Candida albicans*.

TABLE 6

MIC and MBC Data for Cocamidopropyl Betaine Alone

| Organism | MIC[a] | MBC[a] |
|---|---|---|
| P. aeruginosa | 25 | 50 |
| P. mirabilis | 25 | 50 |
| E. coli | 25 | 50 |
| S. intermedius | 0.1 | 0.1 |
| M. pachydermatis | 0.1 | 0.3 |
| C. albicans | 0.1 | 0.3 |

[a]percent of stock solution

TABLE 7

MIC and MBC Data for Tris-EDTA Alone

| Organism | MIC[b] | MBC[b] |
|---|---|---|
| P. aeruginosa | 100 | >100 (125% or 1.25x) |
| P. mirabilis | >100 (500% or 5x) | >100 (1000% or 10x) |
| E. coli | >100 (500% or 5x) | >100 (500% or 5x) |
| S. intermedius | 12.5 | 25 |
| M. pachydermatis | 3.9 | 7.8 |
| C. albicans | 7.8 | 62.5 |

[b]percent of 1x formulation

TABLE 8

MIC And MBC Data For 1x Tris-EDTA Formulation With 10% Cocamidopropyl Betaine

| Organism | MIC[c] | MBC[c] |
|---|---|---|
| P. aeruginosa | 12.5 | 100 |
| P. mirabilis | 25 | >100 (125% or 1.25x) |
| E. coli | 6.25 | 6.25 |
| S. intermedius | <0.2 | <0.2 |
| M. pachydermatis | 3.9 | 3.9 |
| C. albicans | <0.2 | <0.2 |

[c]percent of 1x formulation

The only organism not killed, though its growth was inhibited, by the test cleaner formulation was *Proteus mirabilis*. Based on MIC data, there is synergistic effects for the 1x formulation with 10% cocamidopropyl betaine reacting against *Pseudomonas aeruginosa, Proteus mirabilis*, and *Escherichia coli*.

Example 13

Stability and Antibacterial Activity of EDTA-Tris-Neomycin Solution (ETN) in KY Gel Mixtures were prepared, stored at room temperature, and tested monthly against the test organism *Pseudomonas aeruginosa*. Compositions were prepared with or without KY™ gel. KY™ gel was Sodium Carboxymethylcellulose 7H 4F (Food Grade) (Hercules, Inc., Wilmington, Del.)

Addition of 1% or 2% KY™ gel to the EDTA-Tris-antibiotic compositions did not affect the long term stability and antibacterial activity of the solutions of EDTA-Tris and neomycin, as shown in Table 9.

TABLE 9

Effect of Mixing Ky™ Gel on EDTA-Tris-Neomycin (ETN) Storage Stability
$Log_{10}$ CFU/ml

| | PBS | ETN | ETN + 1% KY gel | ETN + 2% KY gel |
|---|---|---|---|---|
| 1 month | 7.60 | NG | NG | NG |
| 2 months | 7.56 | NG | 4.04 | 4.48 |
| 3 months | 6.78 | NG | NG | 2.00 |
| 4 months | 7.73 | NG | NG | NG |
| 5 months | 6.64 | NG | NG | NG |
| 6 months | 6.94 | NG | NG | NG |
| 7 months | 7.40 | NG | NG | NG |
| 8 months | 7.56 | NG | NG | NG |
| 9 months | 8.00 | NG | NG | NG |
| 10 months | 7.85 | NG | NG | NG |

Example 14

Inhibition of the Growth of Microorganisms Infecting Burns

The organisms of this study were isolated from human burn patients. They included strains of methicillin resistant *Staphylococcus aureus*, and vancomycin resistant strains of *Pseudomonas aeruginosa* and *Enterococcus faecalis*. The bacterial isolates were propagated in or on Brain Heart Infusion broth (BHI), Mueller-Hinton Broth (MHB), blood agar (BA), Mueller-Hinton agar (MHA), *enterococcus* agar (EA), or 2x nutrient agar (2xNA).

The EDTA-Tris treatment solutions were prepared from a stock solution containing 0.5 mols/1 sodium EDTA and 1.0 mols/1 Tris-HCl, pH 8.0. The treatment solutions contained 5 mM sodium EDTA and 50 mM Tris-HCl with or without neomycin sulfate 1 mg/ml.

Antibiotic resistance profiles were determined by the disc diffusion method of MHA. Antibiotics tested included ampicillin (AM-10), chloramphenicol (C-30), ciprofloxacin (CIP-5), kanamycin (K-30), gentamicin (GM-10), nalidixic acid (NA-30), neomycin (N-30), streptomycin (S-10), sulfisoxazole (G-25), tetracycline (The-30), and vancomycin (Va-30).

Minimal Inhibitory Concentrations (MICs) and Minimal Bactericidal Concentrations (MBCs) for EDTA-Tris and neomycin were determined by the broth-dilution microtiter method of MHB or BHI according to the method of Blair et al., *Manual of Clinical Microbiology*, p. 307 (pub: Am. Soc. Microbiol. Williams and Wilkins, Baltimore 1970), incorporated herein by reference in its entirety. The results are shown in Tables 1 and 2.

Example 15

Treatment of a Skin Burn of a Dog and Antimicrobial Protection of Graft Donor Sites by Vitamin E with EDTA-Tris and Antibiotic A mixed-breed, 35 lb spayed female canine, 1-2 years old, had been doused with gasoline, set on fire and burned over 30% of body. The dog was given initial emergency treatment for 5 days and the burned area cultured for microbial infection, identifying: β-hemolytic *E. coli, Klebsiella oxytoca, Proteus* sp., and *Enterococcus* sp. The dog was administered cefazolin systemically and the burned area cleared of tissue debris and wetted with a solution of EDTA-Tris and neomycin daily. The burn area was free of the four bacteria after 3 days of systemic and topical EDTA-Tris-neomycin therapy. After approximately 10 days, neomycin was replaced with amikacin. The dog received an autologous skin graft approximately three weeks after the burn incident and the donor site treated with EDTA-Tris-amikacin and 100 IU of Vitamin E. The dog was discharged from veterinary hospital care two weeks later.

Example 16

Management of a Burn Wound

A first to second degree burn wound on the inner surface of the lower arm of approximately 1 week duration was treated. While the burn was healing, it remained crusty and pruritic. Application of 35 mls. of hydrous lanolin, 15 mls of 333 UI/ml Vitamin E, and 0.73 gms of EDTA, 0.6 gms of Tris dissolved in 2 mls. of distilled water and 0.1 mg/ml of ampicillin resulted in cessation of pruritis within 15 minutes. Repeat application when the wound began to itch resulted in similar cessation of itching.

Example 17

Effect of Combination of Tris, EDTA, and Neomycin on Burn

This Example describes the results of experiments to evaluate the effectiveness of Tris-EDTA and neomycin on a *Pseudomonas aeruginosa* infected, Biobrane treated burn wound.

After establishing standard inoculum, incubation period and treatment modalities, 2 cm$^3$ second degree burns were created in New Zealand white rabbits. Wounds were inoculated with 10$^6$ colony forming units (CFU) of *Pseudomonas aeruginosa*, and allowed to incubate for 24 hours. After the incubation period, wounds were cleaned and dressed with Biobrane® synthetic wound dressing (Bertek Pharmaceuticals, Inc., 781 Chestnut Ridge Road, Morgantown, W. Va. 26505). Rabbits were randomized into three topical treatment groups: Control, Neomycin and Tris/EDTA-Neomycin. The burns were treated for 24 and 196 hrs. Outer dressings were changed daily according to the topical treatment limb of the study.

At the end of the treatment period, burns were excised aseptically, weighed and sent for pathologic and microbiologic analysis. Tissues were homogenized, serially diluted and plated on tryptic soy agar in triplicate. Average CFU/gram of tissue was determined for the three treatment limbs. Pathology samples were analyzed for degree of reepithelialization of the wound. Statistical analysis was performed using two way ANOVA with Tukey Confirmation with statistical significance of $p<0.05$ and a power of 0.9.

Tris-EDTA-Neomycin induced a two log decrease in CFU/gm of tissue as compared with both Control and Neomycin alone ($p<0.001$). Serial dilutions grew only one colony type, *Pseudomonas aeruginosa*. Treatment modalities had no systemic effects on the animals. In clinical observation and in photomicrographs, the Tris/EDTA-Neomycin limb appeared to heal at an improved rate compared to control healing. In pathologic evaluation, however, there was no statistical difference in reepithelialization.

Tris-EDTA potentiates antibiotic topical treatment of infected Biobrane-treated thermal wounds, thereby decreasing bacterial load. Tris-EDTA caused a clinically significant improvement in wound healing.

Example 18

This example describes the results of experiments to determine the antimicrobial effect of cocamidopropyl betaine, the combination of 20 mM Tris and 8 mM EDTA, and the combination of cocamidopropyl betaine, 20 mM Tris and 8 mM EDTA on *Pseudomonas aeruginosa, Proteus mirabilis, Escherichia coli, Staphylococcus intermedius, Malassezia pachydermatis*, and *Candida albicans* isolated from dogs with otitis externa and pyoderma. The results of the experiments are shown in Tables 10-18.

TABLE 10

MIC and MBC Data for Cocamidopropyl Betaine Alone
(1x stock solution of 10% cocamidopropyl betaine)

| | MIC | MBC |
|---|---|---|
| P. aeruginosa | 0.25x | 0.5x |
| P. mirabilis | 0.25x | 0.5x |
| E. coli | 0.25x | 0.5x |
| S. intermedius | 0.001x | 0.001x |
| M. pachydermatis | 0.001x | 0.003x |
| C. albicans | 0.001x | 0.003x |

TABLE 11

MIC and MBC Data for the Combination of Tris and EDTA
(1x stock solution Was 20 mM Tris, 8 mM EDTA)

| | MIC | MBC |
|---|---|---|
| P. aeruginosa | 1.0x | 1.25x |
| P. mirabilis | 5.0x | 10.0x |
| E. coli | 5.0x | 5.0x |
| S. intermedius | 0.125x | 0.25x |
| M. pachydermatis | 0.04x | 0.08x |
| C. albicans | 0.08x | 0.625x |

TABLE 12

MIC and MBC Data for the Combination of Tris, EDTA, and Cocamidopropyl Betaine (1x stock solution was 20 mM Tris, 8 mM EDTA, and 10% cocamidopropyl betaine)

| | MIC | MBC |
|---|---|---|
| P. aeruginosa | 0.125x | 1.0x |
| P. mirabilis | 0.25x | 1.25x |
| E. coli | 0.0625x | 0.0625x |
| S. intermedius | <0.002x | <0.002x |
| M. pachydermatis | 0.039x | 0.039x |
| C. albicans | <0.002x | <0.002x |

TABLE 13

MIC and MBC Data for the Combination of Tris and EDTA
With 1.0, 2.0, 3.0, 4.0, 5.0, 6.0, 8.0, and 10% Cocamidopropyl Betaine
on *Escherichia Coli* Isolated From a Dog With Otitis Externa
(1x stock solution of Tris and EDTA was 20 mM Tris and 8 mM EDTA)

| % Cocamidopropyl betaine | MIC | MBC |
|---|---|---|
| 1 | 0.25x | 0.25x |
| 2 | 0.25x | 0.25x |
| 3 | 0.25x | 0.25x |
| 4 | 0.25x | 0.25x |
| 5 | 0.125x | 0.25x |
| 6 | 0.125x | 0.25x |
| 8 | 0.125x | 0.25x |
| 10 | 0.125x | 0.25x |

TABLE 14

MIC and MBC Data for the Combination of Tris and EDTA
With 1.0, 2.0, 3.0, 4.0, 5.0, 6.0, 8.0, and 10% Cocamidopropyl Betaine
on *Pseudomonas Aeruginosa* Isolated From a Human Burn Patient
(1x stock solution of Tris and EDTA was 20 mM Tris and 8 mM EDTA)

| % Cocamidopropyl betaine | MIC | MBC |
|---|---|---|
| 1 | 0.25x | 1.0x |
| 2 | 0.25x | 1.0x |
| 3 | 0.25x | 1.0x |
| 4 | 0.125x | 1.0x |
| 5 | 0.125x | 1.0x |
| 6 | 0.125x | 1.0x |
| 8 | 0.125x | 1.0x |
| 10 | 0.125x | 1.0x |

TABLE 15

MIC and MBC Data for the Combination of Tris and EDTA
With 1.0, 2.0, 3.0, 4.0, 5.0, 6.0, 8.0, and 10% Cocamidopropyl Betaine
on *Enterococcus Faecalis* Isolated From a Human Burn Patient
(1x stock solution of Tris and EDTA was 20 mM Tris and 8 mM EDTA)

| % Cocamidopropyl betaine | MIC | MBC |
|---|---|---|
| 1 | <0.625x | <0.625x |
| 2 | <0.625x | <0.625x |
| 3 | <0.625x | <0.625x |
| 4 | <0.625x | <0.625x |
| 5 | <0.625x | <0.625x |
| 6 | <0.625x | <0.625x |
| 8 | <0.625x | <0.625x |
| 10 | <0.625x | <0.625x |

TABLE 16

MIC and MBC Data for Combinations of Tris, EDTA, Cocamidopropyl Betaine (Cocam),
and Silver Inoculated With *Pseudomonas Aeruginosa*, *Enterococcus Faecalis*, and
*Staphylococcus Aureus* Isolated From a Human Burn Patients and *Escherichia Coli*
Isolated From a Dog With Otitis Externa

| | P. aeruginosa | | S. aureus | | E. faecalis | | E. coli | |
|---|---|---|---|---|---|---|---|---|
| | MIC | MBC | MIC | MBC | MIC | MBC | MIC | MBC |
| 20 mM Tris, 8 mM EDTA | >0.5x | >0.5x | 0.25x | 0.25x | 0.25x | >0.5x | 5.0x | 5.0x |
| Silver 22 ppm | >0.5x | >0.5x | >0.5x | >0.5x | >0.5x | >0.5x | ND | ND |
| 20 mM Tris, 8 mM EDTA + Silver 22 ppm | 0.5x | 0.5x | 0.25x | 0.25x | 0.25x | >0.5x | ND | ND |
| Cocam (stock) | 0.25x | 0.5x | 0.001x | 0.001x | ND | ND | 0.25x | 0.5x |
| 20 mM Tris, 8 mM EDTA + 1% Cocam | 0.25x | 1.0x | ND | ND | <0.625x | <0.625x | 0.25x | 0.25x |
| Silver 100 ppm | >0.5x | >0.5x | >0.5x | >0.5x | >0.5x | >0.5x | >0.5x | >0.5x |
| 20 mM Tris, 8 mM EDTA + Silver 100 ppm | 0.25x | 0.25x | 0.25x | 0.5x | 0.25x | >0.5x | 0.25x | 0.5x |
| 40 mM Tris, 16 mM EDTA + Silver 100 ppm | 0.25x | 0.25x | 0.125x | 0.5x | 0.125x | >0.5x | 0.5x | 0.5x |
| 10 mM Tris, 8 mM EDTA + Silver 34 ppm + 1% Cocam | 0.25x | 0.5x | 0.03x | 0.03x | 0.02x | 0.03x | 0.25x | 0.25x |

ND = not done

TABLE 17

MIC and MBC Data for Combinations of 20 mM Tris Plus 8 mM EDTA,
1% Cocamidopropyl Betaine (Cocam), 32 ppm Silver Inoculated With *Pseudomonas
Aeruginosa*, *Enterococcus Faecalis*, and *Staphylococcus Aureus*
Isolated From a Human Burn Patient

| | S. aureus | | P. aeruginosa | | E. faecalis | |
|---|---|---|---|---|---|---|
| | MIC | MBC | MIC | MBC | MIC | MBC |
| 20 mM Tris, 8 mM EDTA | 0.25x | 0.5x | >0.5x | >0.5x | 0.25x | >0.5x |
| 32 ppm Silver | >0.5x | >0.5x | 0.125x | 0.25x | 0.5x | >0.5x |
| 20 mM Tris, 8 mM EDTA + 32 ppm Silver | 0.25x | 0.25x | 0.125x | 0.25x | 0.25x | 0.5x |
| 20 mM Tris, 8 mM EDTA + 32 ppm Silver, 1% cocamidopropyl betaine | 0.03125x | 0.03125x | 0.125x | 0.125x | ≤0.0156x | ≤0.0156x |

TABLE 18

MIC and MBC Data for Combinations of 20 mM Tris, 8 mM EDTA, 1% Cocamidopropyl Betaine (Cocam), 32 ppm Silver Solution and 20 mM Tris, 8 mM EDTA in Sovereign Silver (10 ppm) Inoculated With *Pseudomonas Aeruginosa*, *Enterococcus Faecalis*, and *Staphylococcus Aureus* Isolated From a Human Burn Patient

|  | S. aureus | | P. aeruginosa | | E. faecalis | |
| --- | --- | --- | --- | --- | --- | --- |
|  | MIC | MBC | MIC | MBC | MIC | MBC |
| 20 mM Tris, 8 mM EDTA | 0.25x | 0.5x | >0.5x | >0.5x | 0.25x | >0.5x |
| 32 ppm Silver | >0.5x | >0.5x | 0.125x | 0.25x | 0.5x | >0.5x |
| 20 mM Tris, 8 mM EDTA + 32 ppm Silver | 0.25x | 0.25x | 0.125x | 0.25x | 0.25x | 0.5x |
| 20 mM Tris, 8 mM EDTA 32 ppm Silver, 1% cocamidopropyl betaine | 0.03125x | 0.03125x | 0.125x | 0.125x | ≤0.0156x | ≤0.0156x |
| Sovereign Silver 10 ppm | >0.5x | >0.5x | >0.5x | >0.5x | >0.5x | >0.5x |
| 20 mM Tris, 8 mM + Sovereign Silver 10 ppm | 0.25x | 0.25x | 0.25x | 0.25x | 0.25x | >0.5x |

Example 19

Antibacterial and Antifungal Effect of a Tris-EDTA Composition

This example describes the antimicrobial effect of a Tris-EDTA composition that includes cocamidopropyl betaine and silver on a variety of bacteria and fungi.

Ten μl of overnight Brain Heart Infusion broth cultures of *Pseudomonas aeruginosa*, *Escherichia coli*, *Proteus mirabilis*, *Staphylococcus intermedius*, and *Candida albicans* were inoculated into 1.0 ml of PBS and 1.0 ml of a composition containing 20 mM Tris, 8 mM EDTA, cocamidopropyl betaine and silver ions. Ten μl of a 5-day-old Sabouraud Dextrose broth with 1% Tween 80 culture of *Malassezia pachydermatis* was inoculated into 1.0 ml of PBS and 1.0 ml of 20 mM Tris, 8 mM EDTA, cocamidopropyl betaine and silver ions. Ten μl of a spore suspension of *Aspergillus niger* and *Microsporum gypseum* in Sabouraud Dextrose broth was inoculated into 1.0 ml of PBS and 1.0 ml of 20 mM Tris, 8 mM EDTA, cocamidopropyl betaine and silver ions. Mixtures were vortexed and incubated at 25° C. Samples were taken at time 0 and 1, 3, and 5 minutes of incubation. Ten-fold dilutions of the samples were made in PBS and inoculated on appropriate agar media: Plates were incubated overnight at 37° C. for *Pseudomonas aeruginosa*, *Escherichia coli*, *Proteus mirabilis*, *Staphylococcus intermedius*, and *Candida albicans*, four days at 32° C. for *Malassezia pachydermatis*, 2 days at 35° C. for *Aspergillus niger*, and 7 days at 28° C. for *Microsporum gypseum*. Colony counts determined ($Log_{10}$ CFU/ml). The results of the experiment are shown in Table 19.

TABLE 19

|  | Minutes Treatment | | | |
| --- | --- | --- | --- | --- |
|  | 0 | 1 | 3 | 5 |
| S. intermedius | 6.43 Log10 CFU/ml | 4.52 Log10 CFU/ml decrease 98.5% | 3.82 Log10 CFU/ml decrease 99.8% | 4.3 Log10 CFU/ml decrease 99.3% |

TABLE 19-continued

|  | Minutes Treatment | | | |
| --- | --- | --- | --- | --- |
|  | 0 | 1 | 3 | 5 |
| P. aeruginosa | 5.99 Log10 CFU/ml | 0 Log10 CFU/ml decrease 100% | 0 Log10 CFU/ml decrease 100% | 0 Log10 CFU/ml decrease 100% |
| M. pachydermatis | 4.07 Log10 CFU/ml | 3.52 Log10 CFU/ml decrease 71.5% | 0 Log10 CFU/ml decrease 100% | 0 Log10 CFU/ml decrease 100% |
| A. niger* | 6.0 Log10 CFU/ml | 5.0 Log10 CFU/ml decrease 90% | 5.0 Log10 CFU/ml decrease 90% | 5.0 Log10 CFU/ml decrease 90% |
| M. gypseum | 3.0 Log10 CFU/ml | 0 Log10 CFU/ml decrease 100% | 0 Log10 CFU/ml decrease 100% | 0 Log10 CFU/ml decrease 100% |

Example 20

Antimicrobial Activity of a Tris-EDTA Composition on Bacteria Isolated From Human Burn Patients 0.75 grams of a solution of 20 mM Tris, 8 mM EDTA was mixed with ointment in sterile 1.7 ml microcentrifuge tubes. 0.75 grams of ointment was placed in a sterile 1.7 ml microcentrifuge tube without Tris or EDTA. The microcentrifuge tubes were centrifuged for 30 seconds at 5,000×G. The tubes were then inoculated with 7.5 μl of overnite culture of *Staphylococcus aureus*, or *Pseudomonas aeruginosa*, or *Enterococcus faecalis* isolated from human burn patients. The inoculated tubes were incubated overnight at 35° C. 750 μl of phosphate buffered saline (abbreviated as PBS) were added to each tube, the tube was vortexed, and the contents of the tubes were allowed to react for 3 hours at 25° C. Plate counts were performed using appropriate media, and after incubation at 35° C. for 24 hours, the colonies were counted. The results of the experiment are shown in Table 20.

TABLE 20

| | Ointment alone | Ointment With 20 mM Tris, 8 mM EDTA | % Decrease |
|---|---|---|---|
| S. aureus | 6.53 Log10 CFU/ml | 1.86 Log10 CFU/ml | 99.99 |
| P. aeruginosa | 6.51 Log10 CFU/ml | 0.57 Log10 CFU/ml | 99.99 |
| E. faecalis | 5.60 Log10 CFU/ml | 0 Log10 CFU/ml | 100 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of promoting healing of a burn on a mammalian, bird, or reptile body in need thereof, the method comprising applying to said burn an amount of a composition consisting of Tris, EDTA, and dissolved silver in a pharmaceutically acceptable carrier selected from the group consisting of water, saline, physiological saline, an ointment, a cream, an oil-water emulsion, and a gel, wherein the silver, Tris, and EDTA are in amounts sufficient to promote healing of a burn on a mammalian, bird, or reptile body, the composition consisting of a pH of from 6.0 to 9.0, and optionally, a detergent, a vitamin, an anti-inflammatory agent, lecithin, glycerin, methyl paraben, aloe vera, polypropylene glycol ethoxylate, and/or poloxamer 407, effective to promote healing therefor.

2. A method of promoting healing of a wound in, or on, a living mammalian, bird, or reptile body in need thereof, the method comprising applying to or in said wound an amount of a composition consisting of Tris, EDTA, and dissolved silver in a pharmaceutically acceptable carrier selected from the group consisting of water, saline, physiological saline, an ointment, a cream, an oil-water emulsion, and a gel, wherein the silver, Tris, and EDTA are in amounts sufficient to promote healing of a burn on a mammalian, bird, or reptile body, the composition consisting of a pH of from 6.0 to 9.0, and optionally, a detergent, a vitamin, an anti-inflammatory agent, lecithin, glycerin, methyl paraben, aloe vera, polypropylene glycol ethoxylate, and/or poloxamer 407, effective to promote healing therefor.

3. A method of treating a burn in a human subject in need thereof comprising administering to the human subject a therapeutically effective amount of a composition consisting of Tris, EDTA, and dissolved silver in a pharmaceutically acceptable carrier selected from the group consisting of water, saline, physiological saline, an ointment, a cream, an oil-water emulsion, and a gel, wherein the silver, Tris, and EDTA are in amounts sufficient to promote healing of a burn on a mammalian, bird, or reptile body, the composition having consisting of a pH of from 6.0 to 9.0, and optionally, a detergent, a vitamin, an anti-inflammatory agent, lecithin, glycerin, methyl paraben, aloe vera, polypropylene glycol ethoxylate, and/or poloxamer 407, effective to promote healing therefor.

4. A method of treating a wound in a human subject in need thereof comprising administering to the human subject a therapeutically effective amount of a composition consisting of Tris, EDTA, and dissolved silver in a pharmaceutically acceptable carrier selected from the group consisting of water, saline, physiological saline, an ointment, a cream, an oil-water emulsion, and a gel, wherein the silver, Tris, and EDTA are in amounts sufficient to promote healing of a burn on a mammalian, bird, or reptile body, the composition consisting of a pH of from 6.0 to 9.0, and optionally, a detergent, a vitamin, an anti-inflammatory agent, lecithin, glycerin, methyl paraben, aloe vera, polypropylene glycol ethoxylate, and/or poloxamer 407, effective to promote healing therefor.

5. The method according to claim 2 wherein the wound is an ulcer.

6. The method according to claim 4 wherein the wound is an ulcer.

7. The method according to claim 2 wherein the wound is colonized by a bacterium selected from the group consisting of: Aerobacter spp.; Aeromonas spp.; Bacillus spp.; Bordetella spp; Campylobacter spp.; Chlamydia spp.; Corynebacterium spp.; Escherichia spp., Helicobacter pylori; Klebsiella pneumoniae; Legionella pneumophiia; Leptospira spp.; Mycobacterium spp.; Neisseria spp.; Nocardia spp.; Proteus spp.; Pseudomonas aeruginosa; Rhodococcus equi, Salmonella spp.; Shigella spp.; Staphylococcus spp.; Streptococcus spp.; Vibrio spp.; Yersinia spp.; Actinomycetes spp.; Propionibacterium spp.; and Streptomyces spp.

8. The method according to claim 4 wherein the wound is colonized by a bacterium selected from the group consisting of: Aerobacter spp.; Aeromonas spp.; Bacillus spp.; Bordetella spp; Campylobacter spp.; Chlamydia spp.; Corynebacterium spp.; Escherichia spp., Helicobacter pylori; Klebsiella pneumoniae; Legionella pneumophiia; Leptospira spp.; Mycobacterium spp.; Neisseria spp.; Nocardia spp.; Proteus spp.; Pseudomonas aeruginosa; Rhodococcus equi, Salmonella spp.; Shigella spp.; Staphylococcus spp.; Streptococcus spp.; Vibrio spp.; Yersinia spp.; Actinomycetes spp.; Propionibacterium spp.; and Streptomyces spp.

9. The method according to claim 2 wherein the wound is colonized by a fungus selected from the group consisting of Aspergillus spp., Fusarium spp., Mucor spp., Penicillium spp., Trichophyton spp., Microsporum spp., Candida spp., Malessizia spp., Psuedallescheria spp., Paecilomyces spp., Scedosporium spp and Dematiaceous fungi.

10. The method according to claim 4 wherein the wound is colonized by a fungus selected from the group consisting of Aspergillus spp., Fusarium spp., Mucor spp., Penicillium spp., Trichophyton spp., Microsporum spp., Candida spp., Malessizia spp., Psuedallescheria spp., Paecilomyces spp., Scedosporium spp and Dematiaceous fungi.

* * * * *